(12) United States Patent
Iyer et al.

(10) Patent No.: US 8,849,404 B2
(45) Date of Patent: Sep. 30, 2014

(54) FEEDTHROUGH ASSEMBLY INCLUDING A LEAD FRAME ASSEMBLY

(75) Inventors: Rajesh V. Iyer, Eden Prairie, MN (US); Simon E. Goldman, St. Louis Park, MN (US); Thomas P. Miltich, Otsego, MN (US)

(73) Assignee: Medtronic, Inc., Minneapolis, MN (US)

( * ) Notice: Subject to any disclaimer, the term of this patent is extended or adjusted under 35 U.S.C. 154(b) by 414 days.

(21) Appl. No.: 13/308,144

(22) Filed: Nov. 30, 2011

(65) Prior Publication Data

US 2013/0060312 A1 Mar. 7, 2013

Related U.S. Application Data

(60) Provisional application No. 61/530,249, filed on Sep. 1, 2011.

(51) Int. Cl.
| | |
|---|---|
| *A61N 1/02* | (2006.01) |
| *H05K 13/00* | (2006.01) |
| *A61N 1/375* | (2006.01) |
| *H03H 7/01* | (2006.01) |

(52) U.S. Cl.
CPC ............ *H03H 7/0138* (2013.01); *H05K 13/00* (2013.01); *A61N 1/3754* (2013.01)
USPC .......................................................... 607/37

(58) Field of Classification Search
None
See application file for complete search history.

(56) References Cited

U.S. PATENT DOCUMENTS

| | | |
|---|---|---|
| 3,617,830 A | 11/1971 | Perna |
| 3,920,888 A | 11/1975 | Barr |
| 4,148,003 A | 4/1979 | Colburn et al. |
| 4,152,540 A | 5/1979 | Duncan et al. |
| 4,420,652 A | 12/1983 | Ikeno |
| 4,421,947 A | 12/1983 | Kyle |
| 4,424,551 A | 1/1984 | Stevenson et al. |
| 4,991,582 A | 2/1991 | Byers et al. |
| 5,287,076 A | 2/1994 | Johnescu et al. |
| 5,333,095 A | 7/1994 | Stevenson et al. |
| 5,434,358 A | 7/1995 | Glahn et al. |
| 5,440,447 A | 8/1995 | Shipman et al. |
| 5,470,345 A | 11/1995 | Hassler et al. |
| 5,620,476 A | 4/1997 | Truex et al. |

(Continued)

FOREIGN PATENT DOCUMENTS

| | | |
|---|---|---|
| EP | 1977786 A3 | 10/2008 |
| JP | 06120074 A | 4/1994 |

(Continued)

OTHER PUBLICATIONS

U.S. Appl. No. 13/196,661, by Kengo Morioka, filed Aug. 2, 2011.

(Continued)

*Primary Examiner* — Kennedy Schaetzle
*Assistant Examiner* — Erica Lee

(57) ABSTRACT

A feedthrough assembly may include a ferrule defining a ferrule opening, a feedthrough at least partially disposed within the ferrule opening, a capacitive filter array at least partially disposed within the ferrule opening, and a lead frame assembly. The feedthrough may include at least one feedthrough conductive pathway and the capacitive filter array may include at least one filter array conductive pathway. The lead frame assembly may include an electrically conductive lead electrically connecting the at least one feedthrough conductive pathway and the at least one filter array conductive pathway.

20 Claims, 7 Drawing Sheets

(56) References Cited

U.S. PATENT DOCUMENTS

| | | |
|---|---|---|
| 5,650,759 A | 7/1997 | Hittman et al. |
| 5,683,435 A | 11/1997 | Truex et al. |
| 5,685,632 A | 11/1997 | Schaller et al. |
| 5,735,884 A | 4/1998 | Thompson et al. |
| 5,750,926 A | 5/1998 | Schulman et al. |
| 5,751,539 A | 5/1998 | Stevenson et al. |
| 5,759,197 A | 6/1998 | Sawchuk et al. |
| 5,782,891 A | 7/1998 | Hassler et al. |
| 5,825,608 A | 10/1998 | Duva et al. |
| 5,836,992 A | 11/1998 | Thompson et al. |
| 5,866,851 A | 2/1999 | Taylor et al. |
| 5,867,361 A | 2/1999 | Wolf et al. |
| 5,870,272 A | 2/1999 | Seifried et al. |
| 5,896,267 A | 4/1999 | Hittman et al. |
| 5,905,627 A | 5/1999 | Brendel et al. |
| 5,959,829 A | 9/1999 | Stevenson et al. |
| 5,973,906 A | 10/1999 | Stevenson et al. |
| 5,999,398 A | 12/1999 | Makl et al. |
| 6,008,980 A | 12/1999 | Stevenson et al. |
| 6,031,710 A | 2/2000 | Wolf et al. |
| 6,275,369 B1 | 8/2001 | Stevenson et al. |
| 6,351,368 B1 | 2/2002 | Kim |
| 6,414,835 B1 | 7/2002 | Wolf et al. |
| 6,529,103 B1 | 3/2003 | Brendel et al. |
| 6,566,978 B2 | 5/2003 | Stevenson et al. |
| 6,643,903 B2 | 11/2003 | Stevenson et al. |
| 6,660,116 B2 | 12/2003 | Wolf et al. |
| 6,888,715 B2 | 5/2005 | Stevenson et al. |
| 6,920,673 B2 | 7/2005 | Allen et al. |
| 7,035,076 B1 | 4/2006 | Stevenson |
| 7,068,491 B1 | 6/2006 | Burdon et al. |
| 7,196,899 B1 | 3/2007 | Feger et al. |
| 7,199,995 B2 | 4/2007 | Stevenson |
| 7,668,597 B2 | 2/2010 | Engmark et al. |
| 7,725,177 B2 | 5/2010 | Iyer |
| 7,928,818 B2 | 4/2011 | Iyer |
| 8,180,448 B2 * | 5/2012 | Stevenson et al. ............ 607/2 |
| 8,536,468 B2 | 9/2013 | Teske |
| 2002/0027484 A1 | 3/2002 | Stevenson et al. |
| 2007/0060970 A1 | 3/2007 | Burdon et al. |
| 2007/0203529 A1 | 8/2007 | Iyer et al. |
| 2008/0195180 A1 | 8/2008 | Stevenson et al. |
| 2009/0079517 A1 | 3/2009 | Iyer |
| 2009/0079518 A1 | 3/2009 | Iyer |
| 2009/0187229 A1 | 7/2009 | Lavie |
| 2009/0281603 A1 | 11/2009 | Lim |
| 2010/0202096 A1 | 8/2010 | Iyer |
| 2010/0284124 A1 | 11/2010 | Iyer |
| 2011/0029036 A1 | 2/2011 | Yamamoto et al. |
| 2011/0048770 A1 | 3/2011 | Reiterer et al. |
| 2011/0102967 A1 | 5/2011 | Munns et al. |
| 2011/0245644 A1 * | 10/2011 | Stevenson et al. ............ 600/372 |
| 2013/0058003 A1 | 3/2013 | Iyer et al. |

FOREIGN PATENT DOCUMENTS

| | | |
|---|---|---|
| JP | 06244057 A | 9/1994 |
| WO | 9738752 A2 | 10/1997 |
| WO | 2009117599 A2 | 9/2009 |
| WO | 2010129731 A2 | 11/2010 |
| WO | WO 2011014399 A1 | 2/2011 |
| WO | WO 2011025667 A1 | 3/2011 |

OTHER PUBLICATIONS

U.S. Appl. No. 13/196,683, by Kengo Morioka, filed Aug. 2, 2011.
U.S. Appl. No. 13/196,695, by Kengo Morioka, filed Aug. 2, 2011.
U.S. Appl. No. 13/149,600, by Rajesh V. Iyer, filed May 31, 2011.
U.S. Appl. No. 61/530,249, by Rajesh V. Iyer, filed Sep. 1, 2011.
Office Action from U.S. Appl. No. 13/308,136, dated Jan. 31, 2014, 7 pp.
Office Action from U.S. Appl. No. 13/308,222, dated Jan. 31, 2014, 49 pp.
U.S. Appl. No. 13/308,136, by Rajesh V. Iyer, filed Nov. 30, 2011.
U.S. Appl. No. 13/308,222, by Rajesh V. Iyer, filed Nov. 30, 2011.
U.S. Appl. No. 13/346,424, by Rajesh V. Iyer, filed Jan. 9, 2012.
U.S. Appl. No. 13/308,271, by Rajesh V. Iyer, filed Nov. 30, 2011.
U.S. Appl. No. 13/308,313, by Rajesh V. Iyer, filed Nov. 30, 2011.
Response to Ex Parte Quayle Action dated Apr. 18, 2014, from U.S. Appl. No. 13/308,136, filed Apr. 30, 2014, 6 pp.

* cited by examiner

FEEDTHROUGH ASSEMBLY INCLUDING A LEAD FRAME ASSEMBLY

This application claims the benefit of U.S. Provisional No. 61/530,249 to Iyer et al., entitled, "CAPACITIVE FILTERED FEEDTHROUGH ARRAY FOR IMPLANTABLE MEDICAL DEVICE," and filed on Sep. 1, 2011, which is incorporated herein by reference in its entirety.

TECHNICAL FIELD

The disclosure relates to electrical feedthroughs for implantable medical devices.

BACKGROUND

Electrical feedthroughs may provide an electrical pathway between an interior of a hermetically-sealed housing of an electronics device to a point outside the housing. For example, implantable medical devices (IMDs), such as implantable stimulation devices, implantable sensing devices, cardiac pacemakers, implantable cardioverter/defibrillators (ICDs) and neuromodulators, may use one or more electrical feedthroughs to make electrical connections between electrical circuitry within the implantable medical device and leads, electrodes, or sensors external to the device within a patient.

SUMMARY

In general, the disclosure is directed to feedthrough assemblies and techniques for forming feedthrough assemblies. In some examples, the feedthrough assemblies may be used to provide electrical connections between an exterior of a housing of an IMD and an interior of the housing of the IMD. The feedthrough assemblies may be filtered feedthrough assemblies, and may include at least one capacitive filter and/or a capacitive filter array.

In some examples, the disclosure describes a feedthrough assembly that includes a lead frame assembly for making electrical connection between a conductive pathway of a feedthrough and a conductive pathway of a capacitive filter array. Additionally or alternatively, feedthrough assemblies may include a lead frame assembly used for making electrical connection between a perimeter conductive contact of the capacitive filter array and a ferrule of the feedthrough assembly. In some implementations, the lead frame assembly may be configured to maintain physical separation between opposing surfaces of the feedthrough and the capacitive filter array.

In one aspect, the disclosure is directed to a feedthrough assembly that includes a ferrule defining a ferrule opening, a feedthrough at least partially disposed within the ferrule opening, a capacitive filter array at least partially disposed within the ferrule opening, and a lead frame assembly. In some examples, the feedthrough includes at least one feedthrough conductive pathway and the capacitive filter array includes at least one filter array conductive pathway. In accordance with this aspect of the disclosure, the lead frame assembly includes an electrically conductive lead electrically connecting the at least one feedthrough conductive pathway and the at least one filter array conductive pathway.

In another aspect, the disclosure is directed to an implantable medical device that includes a housing defining an opening and a feedthrough assembly disposed in the opening and attached to the housing. In accordance with this aspect of the disclosure, the feedthrough assembly includes a ferrule defining a ferrule opening, a feedthrough at least partially disposed within the ferrule opening, a capacitive filter array at least partially disposed within the ferrule opening, and a lead frame assembly. In some examples, the feedthrough includes at least one feedthrough conductive pathway and the capacitive filter array includes at least one filter array conductive pathway. In accordance with this aspect of the disclosure, the lead frame assembly includes an electrically conductive lead electrically connecting the at least one feedthrough conductive pathway and the at least one filter array conductive pathway.

In an additional aspect, the disclosure is directed to a method that includes attaching a lead frame assembly to a capacitive filter array, positioning the capacitive filter array and the lead frame assembly in a desired position relative to a ferrule and a feedthrough, and attaching the lead frame assembly to the feedthrough to electrically connect a feedthrough conductive pathway to a filter array conductive pathway The details of one or more examples are set forth in the accompanying drawings and the description below. Other features, objects, and advantages of the disclosure will be apparent from the description and drawings, and from the claims.

DETAILED DESCRIPTION

Figure 1:
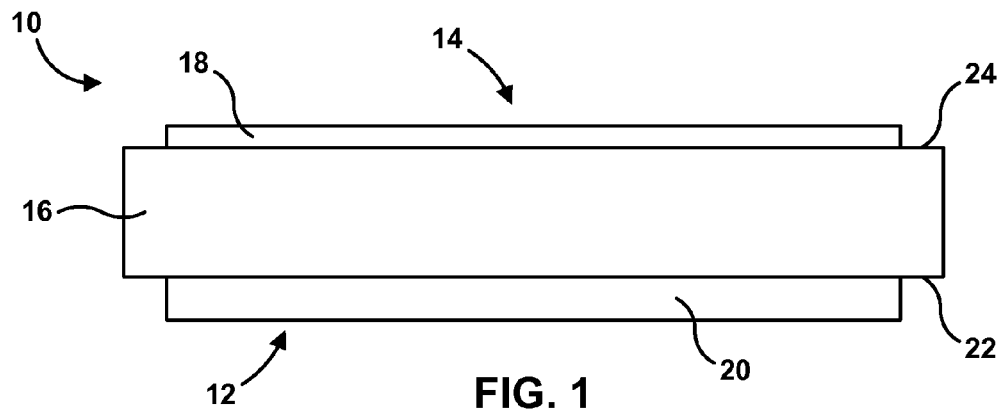
FIG. 1 is a side view that illustrates an example feedthrough assembly.

In some cases, an IMD is implanted at a location within the patient that is different than the target tissue that is being stimulated and/or diagnosed. The IMD may be electrically coupled to a lead that includes electrical conductors that extend from the IMD to the electrodes or sensors located at the target tissue. At the IMD, the electrical conductors may be electrically coupled to a conductive pathway through a feedthrough to allow a lead conductor to be electrically coupled to circuitry contained within the hermetically sealed housing of the IMD. In some examples, the lead conductors may act as antennae that are affected electromagnetic signals, including electromagnetic interference (EMI). The electromagnetic signals may be transmitted along the lead conductor, through the feedthrough, and to circuitry within the IMD. In some cases, the electromagnetic signals may interfere with normal operation of circuitry within the IMD.

EMI due to stray electromagnetic signals conducted by the lead conductors may be addressed by utilizing a capacitor with the feedthrough to form a filtered feedthrough assembly. The capacitor may act as a low-pass filter, transmitting relatively high frequency electromagnetic signals to ground (e.g., the housing of the IMD) and passing relatively low frequency signals to circuitry within the IMD. In some examples, the feedthrough assembly may include a multi-conductor feedthrough and a capacitor or capacitor array that accommodates multiple lead conductors. The capacitor or capacitor array may be attached to the multi-conductor feedthrough so that each of the conductive pathways through the multi-conductor feedthrough is electrically coupled to a corresponding conductive path in the capacitor or capacitor array while providing for a hermetic seal around each conductive pathway and between the multi-conductor feedthrough and the ferrule.

In other examples, an IMD may include one or more electrodes formed on a housing of the IMD (e.g., a leadless IMD). In some implementations, a leadless IMD may include a feedthrough assembly through which a conductor that connects the electrodes formed on the housing of the IMD to circuitry within the leadless IMD passes. The feedthrough assemblies described herein may also be utilized in leadless IMDs.

This disclosure describes various feedthrough assemblies and techniques for forming feedthrough assemblies. The feedthrough assemblies generally may include a feedthrough, a capacitive filter array, and a ferrule. In some examples, the disclosure describes feedthrough assemblies that include a thick film conductive paste for making electrical connection between a conductive pathway of the feedthrough and a conductive pathway of the capacitive filter array. Additionally or alternatively, feedthrough assemblies may include a thick film conductive paste used for making electrical connection between a perimeter conductive contact of the capacitive filter array and the ferrule. In some implementations, the thick film conductive paste may include a silver-palladium (Ag—Pd) alloy or mixture and, optionally, glass frit.

In some examples, the disclosure described a feedthrough assembly that includes a lead frame assembly for making electrical connection between a conductive pathway of the feedthrough and a conductive pathway of the capacitive filter array. Additionally or alternatively, feedthrough assemblies may include a lead frame assembly used for making electrical connection between a perimeter conductive contact of the capacitive filter array and the ferrule. In some implementations, the lead frame assembly may be configured to maintain physical separation between opposing surfaces of the feedthrough and the capacitive filter array.

In some examples, the disclosure described a feedthrough assembly that includes an electrically insulating material disposed between an externally-facing side of a capacitive filter array and an internally-facing side of a feedthrough. In some examples, the electrically insulating material extends substantially continuously between the externally-facing side of the capacitive filter array and the internally-facing side of the feedthrough. In some implementations, the electrically insulating material may be introduced into a gap between the externally-facing side of the capacitive filter array and the internally-facing side of the feedthrough through an underfill access channel. The underfill access channel may be defined in the feedthrough, the capacitive filter array, or a ferrule of the feedthrough assembly. In some examples, the electrically insulating material may be introduced through the underfill access channel into the gap between the externally-facing side of the capacitive filter array and the internally-facing side of the feedthrough after the feedthrough, the ferrule, and the capacitive filter array have been attached to each other.

Figure 2:
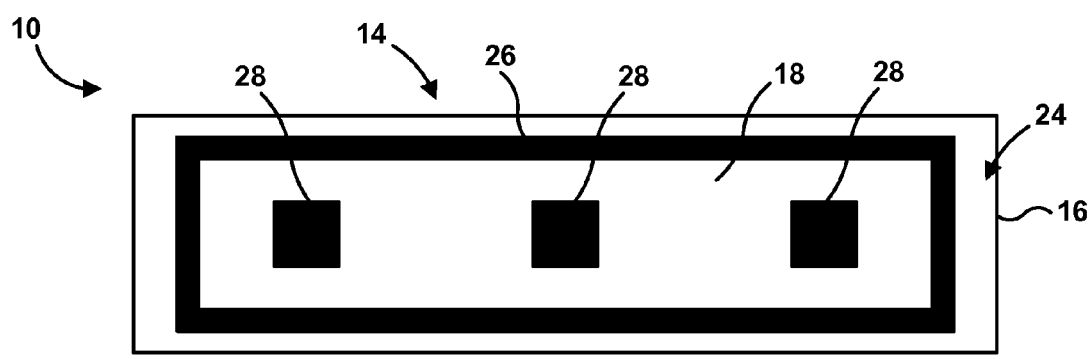
FIG. 2 is a top view that illustrates an example feedthrough assembly.
Figure 3:
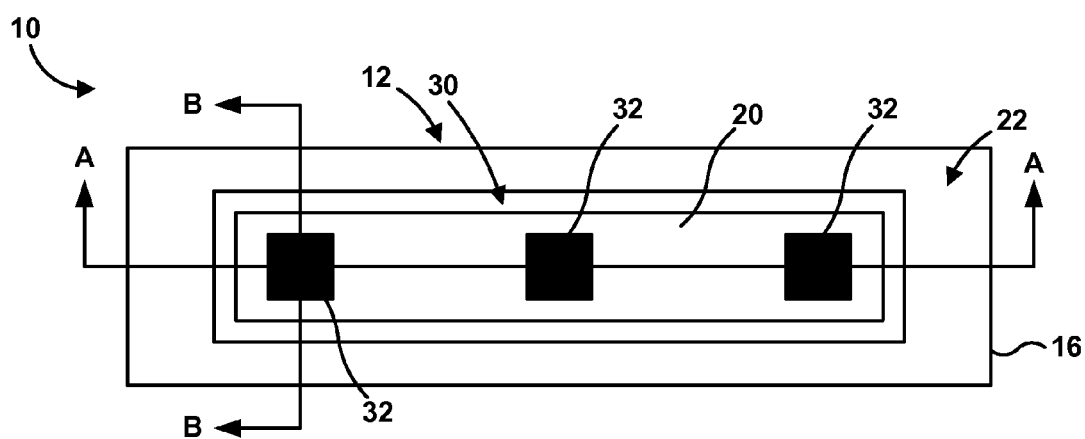
FIG. 3 is a bottom view that illustrates an example feedthrough assembly.

FIG. 1 is a side view of an example feedthrough assembly 10. Feedthrough assembly 10 includes an internally-facing side 12 and an externally-facing side 14. FIG. 2 shows a top view of feedthrough assembly 10 showing the externally-facing side 14 of feedthrough assembly 10. FIG. 3 shows a bottom view of feedthrough assembly 10 showing internally-facing side 12 of feedthrough assembly 10. The terms "internally-facing," "inwardly," and the like, when used herein in regards to feedthrough assembly 10, may generally refer to a direction toward the interior of an electronics device (e.g., an IMD) when assembly 10 is incorporated in the electronics device. Conversely, the terms "externally-facing," "outwardly," and the like, when used herein in regards to feedthrough assembly 10 generally refer to a direction toward the exterior of the electronics device when assembly 10 is incorporated in the electronics device.

As shown in FIGS. 1-3, feedthrough assembly 10 comprises a ferrule 16, a feedthrough 18, and a capacitive filter array 20. Feedthrough 12 may be coupled to capacitive filter array 20 by a plurality of electrically conductive members. The electrically conductive members may take a variety of forms, and will be described in detail below.

Ferrule 16 comprises an internally-facing ferrule side 22 and an externally facing ferrule side 24. Ferrule 16 also defines a ferrule opening 30 that extends between internally-facing side 22 and externally-facing side 24. Feedthrough 12 and capacitive filter array 20 are at least partially disposed in ferrule opening 30. Ferrule 16 may be configured to be mounted to or within the housing of the electronics device, such as an IMD. In some examples, ferrule 16 may include a flange or other mechanical feature that facilitates mounting of ferrule 16 to or within the housing of the electronics device. Ferrule 16 may be mounted to the IMD housing, for example, by welding or brazing.

In one example, ferrule 16 comprises a material that facilitates mounting of ferrule 16 to the housing of an IMD. For example, the IMD housing may comprise titanium or a titanium alloy, and ferrule 16 may comprise titanium or a titanium alloy that can be welded to the IMD housing. Examples of materials from which ferrule 18 may be formed include niobium; titanium; titanium alloys such as titanium-6Al-4V or titanium-vanadium; platinum; molybdenum; zirconium; tantalum; vanadium; tungsten; iridium; rhodium; rhenium; osmium; ruthenium; palladium; silver; and alloys, mixtures, and combinations thereof. In one example, the material from which ferrule 16 is formed is selected so that ferrule 16 has a coefficient of thermal expansion (CTE) that is compatible with the CTE of feedthrough 18. In this manner, damage resulting from the heating of ferrule 16 and feedthrough 18, such as during the formation of a diffusion bonded, glassed, or brazed joint between ferrule 16 and feedthrough 18, may be reduced or substantially prevented.

Feedthrough 18 may be mounted to ferrule 16 within ferrule opening 30 using a hermetic seal 26 formed between feedthrough 18 and ferrule 16. Hermetic seal 26 may prevent bodily fluids of the patient from passing into the interior of IMD housing between ferrule 16 and feedthrough 18, which could lead to damage to the internal electronics of the IMD. In one example, hermetic seal 26 comprises a braze joint between feedthrough 18 and ferrule 16 (e.g., formed using laser brazing). In other examples, hermetic seal 26 may be formed using diffusion bonding. Examples of materials that may be used to form a hermetic seal 26 include any biocompatible, biostable material capable for forming a hermetic seal 26, such as, gold, a nickel-gold alloy, platinum, and platinum-iridium. Laser sintering of glass may also be used to bond feedthrough 18 to ferrule 16.

Figure 4A:
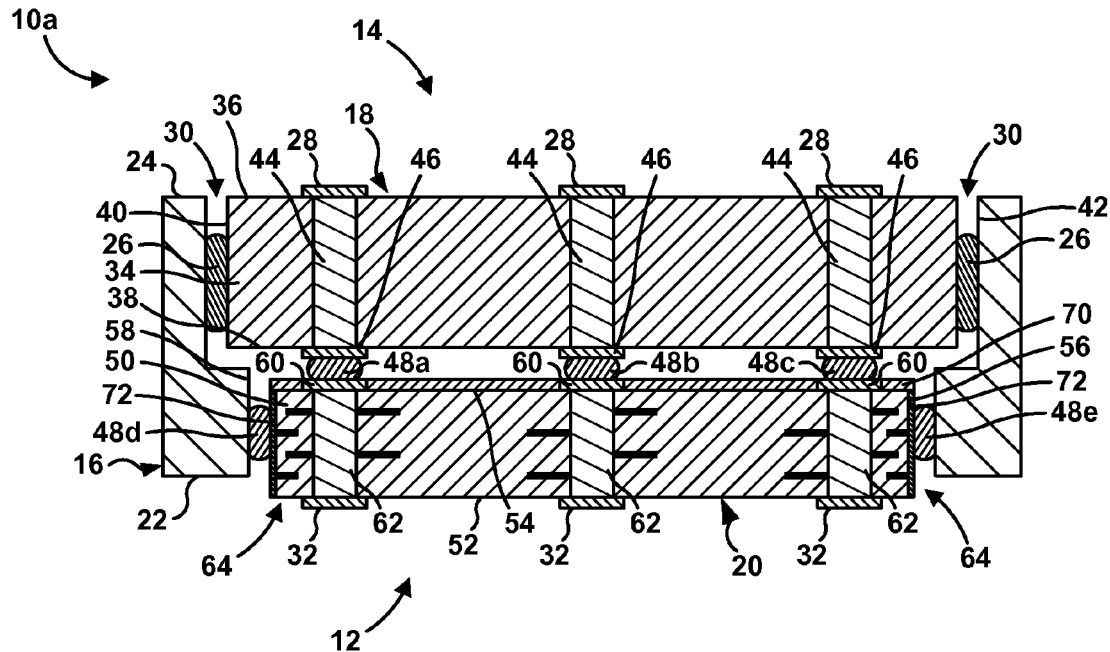
FIGS. 4A and 4B are a cross-sectional views taken along section lines A-A and B-B of FIG. 3 that illustrate an example configuration of a feedthrough assembly.
Figure 4B:
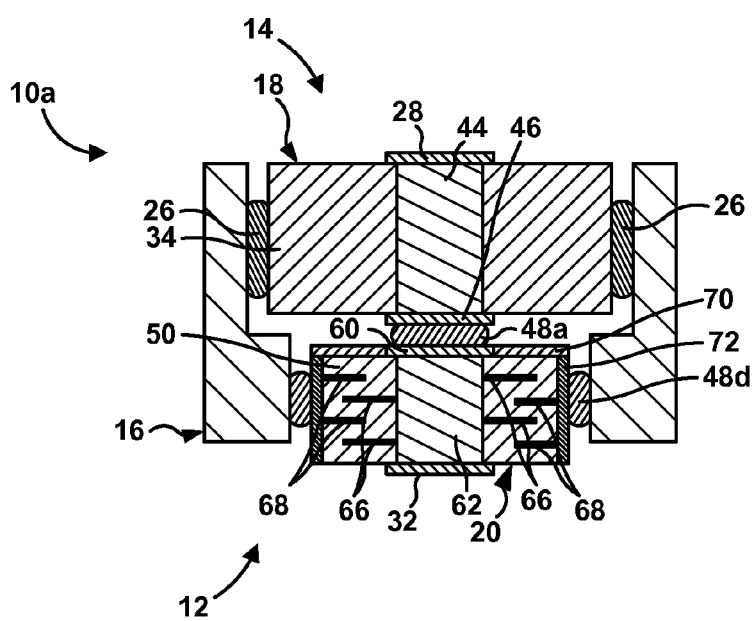

FIGS. 4A and 4B are cross-sectional views of an example feedthrough assembly 10*a* taken along section lines A-A and B-B shown in FIG. 3, respectively. As shown in FIGS. 4A and 4B, feedthrough 18 includes a feedthrough substrate 34. Feedthrough substrate 34 defines an externally-facing feedthrough side 36 and an internally-facing feedthrough side 38. Externally-facing feedthrough side 36 is oriented generally opposite to internally-facing feedthrough side 38. Feedthrough substrate 34 also defines a feedthrough substrate perimeter wall 40, which is oriented facing a first interior wall 42 of ferrule 16. Feedthrough 18 also includes a plurality of feedthrough conductive vias 44, which each extend between externally-facing feedthrough side 36 and internally-facing feedthrough side 38. Each of conductive vias 44 is electrically and physically coupled to a respective one of externally-facing feedthrough conductive pads 28 and a respective one of internally-facing feedthrough conductive pads 46. Externally-facing feedthrough conductive pads 28 may be disposed on or near externally-facing feedthrough side 36. Internally-facing feedthrough conductive pads 46 may be disposed on or near internally-facing feedthrough side 38. Each of feedthrough conductive vias 44 may be substantially electrically isolated from the other feedthrough conductive vias 44. Although FIG. 4A shows an example in which feedthrough 18 includes three externally-facing feedthrough conductive pads 28, three feedthrough conductive vias 44, and three internally-facing feedthrough conductive pads 46, in other examples, feedthrough 18 may include fewer or more externally-facing feedthrough conductive pads 28, feedthrough conductive vias 44, and internally-facing feedthrough conductive pads 46 (e.g., one, two, or at least four).

In some examples, feedthrough substrate 34 comprises a ceramic material formed from a single layer. In other examples, feedthrough substrate 34 includes multi-layer ceramic formed from a plurality of generally planar ceramic layers (not shown in FIGS. 4A and 4B). In examples in which feedthrough substrate 34 is formed from multiple ceramic layers, each ceramic layer may be shaped in a green state to have a layer thickness and a plurality of via holes extending there through between an internally facing layer surface and an externally facing layer surface. The ceramic layers then may be coupled together, such as by laminating the layers together, and may be cofired together so that the layers form a substantially monolithic feedthrough substrate 34. In some examples, the via holes of each ceramic layer may be substantially aligned to form generally cylindrical passages that are filled with an electrically conductive material to form conductive vias 44.

In some examples, feedthrough 34 may comprise a high-temperature cofired ceramic (HTCC) material, e.g., a ceramic that is sintered at a temperature of at least about 1300° C., for example a material that is sintered at a temperature of at least about 1600° C. In some embodiments, HTCC uses 1) an electrical insulator that includes alumina and may include oxides of Si (silica), Ca (calcium), Mg (magnesia), Zr (zirconia), and the like, and 2) an electrical conductor, such as platinum or Pt—Ir. The assembly of the electrical insulator and electrical conductor can be fired (sintered) above 1000° C., such as about 1600° C. In this sintering process, polymeric binders may be driven off and the particles forming the ceramic and metal coalesce and fuse. Grains may diffuse together forming larger grains at the expense of smaller grains.

In one example, feedthrough substrate 34 comprises an HTCC liquid-phase, sintered alumina with platinum metallization. In one example, feedthrough substrate 34 may comprise at least about 70% alumina, for example at least about 90% alumina having a sintering temperature of between about 1550° C. and about 1600° C. In some examples, feedthrough substrate 34 consists essentially of a HTCC, and in some examples, feedthrough substrate 34 consists of a HTCC.

Examples of materials and methods for making a cofired ceramic substrate are described in the commonly assigned U.S. Provisional Patent Application Ser. No. 61/530,249, filed on Sep. 1, 2011; the commonly assigned U.S. Provisional Patent Application Ser. No. 61/238,515, filed on Aug. 31, 2009; the commonly assigned U.S. patent application Ser. No. 12/693,772, filed on Jan. 26, 2010, the commonly assigned U.S. Pat. No. 6,414,835, issued on Jul. 2, 2002, the commonly-assigned U.S. Pat. No. 6,660,116, issued on Dec. 9, 2003, U.S. patent application Ser. No. 13/196,661, filed on Aug. 2, 2011, U.S. patent application Ser. No. 13/196,683, filed on Aug. 2, 2011, and U.S. patent application Ser. No. 13/196,695, filed on Aug. 2, 2011, the entire disclosures of which are incorporated herein by reference.

Conduction of electrical signals between externally-facing feedthrough side 36 and internally-facing feedthrough side 38 may be accomplished using externally-facing feedthrough conductive pads 28, electrically conductive vias 44 and internally-facing feedthrough conductive pads 46. Together, a respective one of externally-facing feedthrough conductive pads 28, a respective one of electrically conductive vias 44, and a respective one of internally-facing feedthrough conductive pads 46 form a feedthrough conductive pathway between externally-facing feedthrough side 36 and internally-facing feedthrough side 38. The electrically conductive pathways provide for an electrical pathway for electrical signals to be transmitted across feedthrough substrate 34, such as stimulation signals transmitted from electronics within an IMD housing for stimulation of a target tissue, or bioelectric signals sensed proximate a target tissue that are transmitted into the IMD housing for analysis by IMD electronics.

Electrically conductive vias 44 may comprise a conductive material, such as a metal or alloy, that substantially fills a passageway that extends through feedthrough substrate 34. In one example, a hermetic seal is formed at the interface between each of electrically conductive vias 44 and feedthrough substrate 34. The hermetic seal may be formed by many methods, such as by forming a braze joint between the material that forms via 44 and the material that forms feedthrough substrate 34. In one example, described in more detail below, the hermetic seal is formed by cofiring the materials that form feedthrough substrate 34 and electrically conductive vias 44 so that the material that forms vias 44 bonds with the material that forms feedthrough substrate 34.

Each electrically conductive pathway also may include an internally-facing feedthrough conductive pad 46 at internally-facing side 38. Each conductive pad 46 may provide a contact area to provide for electrical and/or mechanical coupling between the respective electrically conductive pathway and a respective one of the electrically conductive pathways in capacitive filter array 20. In some examples, each internally-facing feedthrough conductive pad 46 is electrically and mechanically coupled to a corresponding one of electrically conductive vias 44.

Each electrically conductive pathway may also include an externally-facing feedthrough conductive pad 28 at externally-facing side 36. Each conductive pad 28 may provide contact area to provide for electrical and/or mechanical coupling of a conductor, such as a lead conductor for an IMD, to the respective electrically conductive pathway (e.g., the conductive pad 28). In some examples, each externally-facing feedthrough conductive pad 28 is electrically and mechanically coupled to a corresponding one of vias 44.

In some examples, vias 44 and conductive pads 28, 46 each include an electrically conductive material, such as an electrically conductive metal or alloy. Examples of electrically conductive materials that may be used for vias 44 and/or conductive pads 28, 46 include, but are not limited to, transition metals (e.g., noble metals), rare earth metals (e.g., actinide metals and lanthanide metals), alkali metals, alkaline-earth metals, and rare metals. Examples of materials that may be used to form vias 44 and/or conductive pads 28, 46 include, but are not limited to, copper (Cu), silver (Ag), gold (Au), platinum (Pt), palladium (Pd), niobium (Nb), iridium (Ir), titanium (Ti), tungsten (W), molybdenum (Mb), zirconium (Zr), osmium (Os), tantalum (Ta), vanadium (V), rhodium (Rh), rhenium (Re), and ruthenium (Ru), platinum-gold alloys, platinum-iridium alloys, platinum-palladium alloys, gold-palladium alloys, titanium alloys, such as Ti-6Al-4V, Ti-45Nb, Ti-15Mo or titanium-vanadium, tungsten-molybdenum alloys, and alloys, mixtures, and combinations thereof.

With respect to internally-facing feedthrough conductive pads 46, in some examples, the material and structure of conductive pads 46 may be selected to support bonding of a corresponding electrical connection (such as one of thick film conductive paste 48) to provide electrical and mechanical coupling between respective ones of internally-facing feedthrough conductive pad 46 and respective ones of externally-facing filter conductive pads 60.

With respect to externally-facing feedthrough conductive pads 28, the material and structure of conductive pads 28 may be selected to support welding of a conductor, such as a wire or conductor used in a lead for an IMD, to external surfaces of respective ones of conductive pads 28. Examples of materials that may be used in an IMD lead conductor that may be welded to conductive pads 28 include, but are not limited to, niobium (Nb), a MP35N or MP35NLT nickel-based alloy, silver core Co—Cr—Ni alloy, tantalum, silver core Ta, Ti, Ti-45Nb, Ti—Mo alloys, and alloys meeting ASTM standard F562. Examples of processes that may be used to attach the lead conductor to conductive pads 28 include, but are not limited to, laser welding, parallel gap welding, thermosonic bonding, diffusion bonding, ultrasonic welding, opposed gap welding, laser brazing, step gap resistance welding, brazed interposer, percussion arc welding, or soldering (conventional or laser).

In some examples in which feedthrough substrate 34 comprises a HTCC material, conductive vias 44 and/or externally-facing feedthrough conductive pads 28 and/or internally-facing feedthrough conductive pads 46 may include a conductive paste that is used to fill passageways extending from externally-facing feedthrough side 36 and internally-facing feedthrough side 38 to form vias 44. The conductive paste may comprise, for example, a metallic paste that is applied to the passageways, for example a platinum-containing paste, a tungsten-containing paste, Nb-containing paste, Ta-containing paste, Au-containing paste, or a molymanganese-containing paste. Such materials may be biocompatible and biostable materials. In one example, the metallic paste primarily comprises a metallic powder, such as platinum powder, and an additive to promote bonding with the material of feedthrough substrate 34. The additive may additionally or alternatively provide for thermal expansion compatibility between the conductive paste used to form vias 44 (and/or pads 28, 46) and the HTCC material of feedthrough substrate 34. In one example, the additive comprises alumina, so that the metallic paste may comprise, for example, a majority of metallic powder, such as platinum powder, and a minority of alumina powder or particles mixed therein.

In some examples, conductive vias 44 and/or pads 28, 46 formed from a conductive paste, such as a platinum and alumina containing paste, and a feedthrough substrate 34 comprising an HTCC material, such as a sintered alumina, are cofired together, e.g., at a temperature of around 1600° C., so that the conductive paste and HTCC material bond together and form hermetic seal.

Referring still to FIGS. 4A and 4B, feedthrough assembly includes capacitive filter array 20. Capactive filter array 20 may include a capacitive filter substrate 50 that defines an internally-facing filter array side 52 and an externally-facing filter array side 54. Capacitive filter substrate 50 also defines a capacitive filter perimeter 56, which generally faces a second interior wall 58 of ferrule 16. Disposed along a perimeter of capacitive filter substrate is a perimeter conductive contact 72. Capacitive filter array 20 further includes a plurality of filter array conductive pathways. In the example illustrated in FIGS. 4A and 4B, each of the filter array conductive pathways includes a respective one of externally-facing filter conductive pads 60, a respective one of filter conductive vias 62, and a respective one of internally-facing filter conductive pads 32. Respective filter array conductive pathways may be substantially electrically isolated from the other filter array conductive pathways. Although FIG. 4A illustrates an example capacitive filter array 20 that includes three filter array conductive pathways, in other examples, capacitive filter array 20 may include fewer or more than three filter array conductive pathways (e.g., one, two, or at least four).

Capacitive filter array 20 further includes a plurality of capacitive filters 64 defined within capacitive filter substrate 50, respective ones of which are electrically connected to respective ones of the filter array conductive pathways. Each of the plurality of conductive pathways provide an electrical pathway for electrical signals to be transmitted through capacitive filter array 20, such as stimulation signals transmitted from electronics within an IMD housing for stimulation of a target tissue or bioelectric signals sensed proximate a target tissue that are transmitted into the IMD housing for analysis by IMD electronics. Capacitive filter array 20 filters the electrical signals transmitted through capacitive filter array 20 using capacitive filters 64.

Capacitive filter substrate 50 may be formed of a ceramic material, such as barium titanate ($BaTiO_3$) or alumina. In some examples, capacitive filter substrate 50 may be formed from a single layer. In other examples, capacitive filter substrate 50 includes a multi-layer ceramic formed from a plurality of generally planar ceramic layers (not shown in FIGS. 4A and 4B). In examples in which capacitive filter substrate 50 is formed from multiple ceramic layers, each ceramic layer may be shaped in a green state to have a layer thickness and a plurality of via holes extending there through between an internally facing layer surface and an externally facing layer surface. The ceramic layers then may be coupled together, such as by laminating the layers together, and may be cofired together so that the layers form a substantially monolithic capacitive filter substrate 50. In some examples, the passageways of each ceramic layer may be substantially aligned to form generally cylindrical passages that are filled with an electrically conductive material to form conductive vias 62.

In some examples, capacitive filter substrate 50 may comprise a high-temperature cofired ceramic (HTCC) material, e.g., a ceramic that is sintered at a temperature of at least about 1300° C., for example a material that is sintered at a temperature of at least about 1600° C. In some embodiments, HTCC uses 1) an electrical insulator that includes barium titanate (BaTiO$_3$) or alumina and may include oxides of Si (silica), Ca (calcium), Mg (magnesia), Zr (zirconia), and the like and 2) an electrical conductor, such as platinum or Pt—Ir. The assembly of the electrical insulator and electrical conductor can be fired (sintered) above 1000° C., such as about 160° C. In this sintering process, polymeric binders may be driven off and the particles forming the ceramic and metal coalesce and fuse. Grains may diffuse together forming larger grains at the expense of smaller grains.

Capacitive filter array 20 also includes a plurality of filter array conductive pathways. As described above, each filter array conductive pathway includes a respective one of externally-facing filter conductive pads 60, a respective one of filter conductive vias 62, and a respective one of internally-facing filter conductive pads 32. Filter conductive vias 62 and conductive pads 32, 60 each may include an electrically conductive material, such as an electrically conductive metal or alloy. Examples of electrically conductive materials that may be used for vias 62 and/or conductive pads 32, 60 include, but are not limited to, transition metals (e.g., noble metals), rare earth metals (e.g., actinide metals and lanthanide metals), alkali metals, alkaline-earth metals, and rare metals. Examples of materials that may be used to form vias 62 and/or conductive pads 32, 60 include, but are not limited to, copper (Cu), silver (Ag), gold (Au), platinum (Pt), palladium (Pd), niobium (Nb), iridium (Ir), titanium (Ti), tungsten (W), molybdenum (Mb), zirconium (Zr), osmium (Os), tantalum (Ta), vanadium (V), rhodium (Rh), rhenium (Re), and ruthenium (Ru), platinum-gold alloys, platinum-iridium alloys, platinum-palladium alloys, gold-palladium alloys, titanium alloys, such as Ti-6Al-4V, Ti-45Nb, Ti-15Mo or titanium-vanadium, tungsten-molybdenum alloys, and alloys, mixtures, and combinations thereof.

With respect to externally-facing filter conductive pads 60, in some examples, the material and structure of conductive pads 60 may be selected to support bonding of a corresponding electrical connection (such as one of thick film conductive paste 48) to provide electrical and mechanical coupling between respective ones of internally-facing feedthrough conductive pads 46 and respective ones of externally-facing filter conductive pads 60.

With respect to internally-facing filter conductive pads 32, in some examples, the material and structure of conductive pads 32 may be selected to support an electrical connection to a corresponding electrical conductor that extends between internally-facing filter conductive pads 32 and circuitry of the IMD (e.g., sensing circuitry, therapy delivery circuitry, or the like).

In some examples, an electrical insulation layer 70 may be placed between feedthrough 18 and filter array 20 in order to reduce or prevent high-voltage arcing between feedthrough 18 and filter array 20. Electrical insulation layer 70 may also be provided to prevent arcing between the conductive path (which may be continuous between the externally-facing feedthrough conductive pads 28 and filter array 20) and ferrule 16, between the conductive path and perimeter conductive contact 72, or between adjacent conductive paths, as any direct line of sight between the conductive two electrically conductive materials may cause surface arcing. In this sense, electrical insulation layer 70 may reduce or substantially prevent surface arcing.

Electrical insulation layer 70 may include an electrically insulating material, such as an electrically insulating polymer formed on externally-facing filter array side 54. In one example, electrical insulation layer 70 comprises a polyimide polymer with a glass transition temperature of greater than about 400° C. In some examples, electrically insulating layer 70 may comprise a low temperature cofired ceramic material or a HTCC material.

Figure 8:
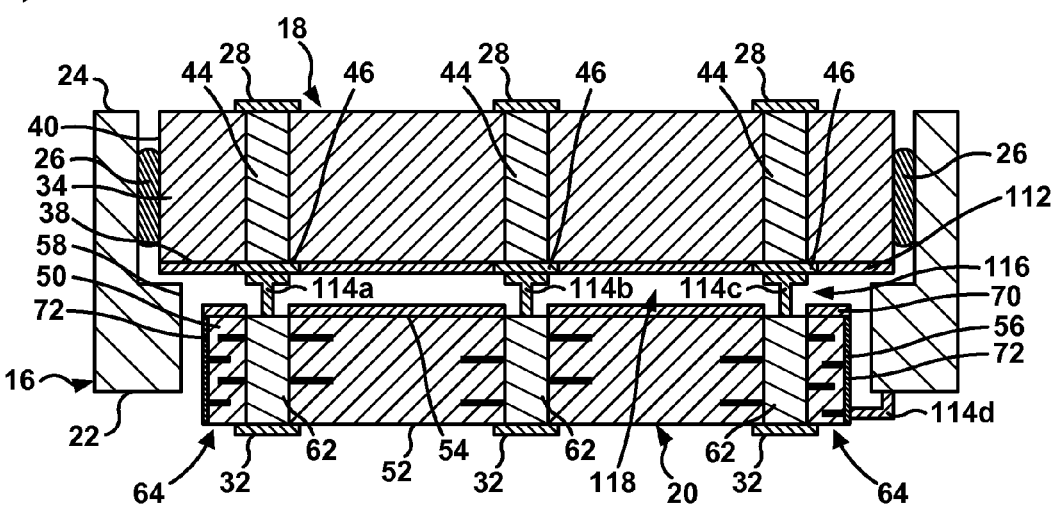
FIG. 8 is a cross-sectional view taken along section line A-A of FIG. 3 that illustrates an example configuration of a feedthrough assembly.

Although not shown in FIGS. 4A and 4B, in some examples, electrically insulating layer 70 may additionally or alternatively be formed on internally-facing feedthrough side 38 (e.g., as embodied by feedthrough electrically insulating layer 112 of FIG. 8), internally-facing filter array side 52, and/or externally-facing feedthrough side 36. In some examples, as described below with respect to FIGS. 10-12, an electrically insulating layer may extend substantially continuously in the space between externally-facing filter array side 54 and internally-facing feedthrough side 38.

At least a portion of each of filter conductive vias 62 is electrically connected to a corresponding capacitive filter 64 that provides for filtering of electrical signals that are conducted through the corresponding via 62. For example, each capacitive filter 64 may provide for filtering of current induced in an IMD lead by external electromagnetic fields so that the induced current is not inadvertently interpreted by the IMD circuitry as a signal, such as a telemetry signal. In one example, best seen in FIG. 4B, each capacitive filter 64 comprises a plurality of layers (not shown) of ceramic, such as barium titanate, with conductive active electrodes 66 and ground electrodes 68 formed on the layers, such as by printing the material of electrodes 66, 68, for example silver, silver-palladium, or silver-platinum, onto the layers before stacking and laminating the layers. In one example, active electrodes 66 substantially radially surround a corresponding one of filter conductive vias 62. Respective active electrodes 66 are electrically coupled to respective filter conductive vias 62. Ground electrodes 68 are electrically connected to a common ground.

Ground electrodes 68 may be electrically coupled to a perimeter conductive contact 72. Perimeter conductive contact 72 may extend substantially along the entire length of capacitive filter perimeter 56, as shown in FIGS. 4A and 4B, so that each ground electrode 68 is electrically coupled to perimeter conductive contact 72. In other examples, perimeter conductive contact 72 may be discontinuous about capacitive filter perimeter 56. For example, a respective perimeter conductive contact 72 may be electrically coupled to a respective one of ground electrodes 68 (or a respective set (two or more) of ground electrodes 68), and capacitive filter array 20 may include a plurality of perimeter conductive contacts 72.

Perimeter conductive contact 72 is electrically coupled to a common ground so that the EMI signals being filtered by capacitive filter array 20 are grounded. In some examples, shown in FIGS. 4A and 4B, perimeter conductive contact 72 is grounded by being electrically coupled to ferrule 16, which in turn is electrically coupled to the IMD housing.

In accordance with some aspects of the disclosure, perimeter conductive contact 72 may be electrically and mechanically connected to ferrule 16 using a thick film conductive paste 48e, 48f. Additionally or alternatively, interior-facing feedthrough conductive pads 46 may be electrically and mechanically connected to exterior-facing filter conductive pads 60 using thick film conductive paste 48a, 48b, 48c. Hence, in some examples, perimeter conductive contact 72 may be electrically and mechanically connected to ferrule 16 using thick film conductive paste 48e, 48f, and interior-facing feedthrough conductive pads 46 may be electrically and mechanically connected to exterior-facing filter conductive pads 60 using thick film conductive paste 48a, 48b, 48c. In other examples, perimeter conductive contact 72 may be electrically and mechanically connected to ferrule 16 using thick film conductive paste 48e, 48f, and interior-facing feedthrough conductive pads 46 may be electrically and mechanically connected to exterior-facing filter conductive pads 60 using another electrically conductive connection, such as a solder connection. In other examples, perimeter conductive contact 72 may be electrically and mechanically connected to ferrule 16 using an electrically conductive connection, such as solder or brazing, and interior-facing feedthrough conductive pads 46 may be electrically and mechanically connected to exterior-facing filter conductive pads 60 using thick film conductive paste 48a, 48b, 48c.

In some examples, thick film conductive paste 48a, 48b, 48c, 48d, 48e (collectively, "thick film conductive paste 48") may include a silver-palladium (Ag—Pd) mixture or alloy. In some implementations, the Ag—Pd mixture or alloy may include about 70 weight percent (wt. %) Ag and about 30 wt. % Pd. In some examples, the Ag—Pd mixture or alloy may also include glass frit (e.g., glass particles mixed in the Ag—Pd mixture or alloy). In some examples, the glass frit includes a zinc borosilicate glass particles, and may be dispersed in an organic binder.

Thick film conductive paste 48 may be applied to any desired thickness. In some examples, the thickness of at least one of thick film conductive paste 48a, 48b, 48c, 48d, 48e is about 0.00254 millimeters (mm; (about 0.0001 inch).

In some examples, thick film conductive paste 48 may form the only mechanical connections between feedthrough 18 and capacitive filter array 20 and/or between capacitive filter array 20 and ferrule 16. Thick film conductive paste 48 may possess sufficient mechanical strength to function as the only mechanical connection between feedthrough 18 and capacitive filter array 20 and between capacitive filter array 20 and ferrule 16 (e.g., after firing to convert thick film conductive paste 48 from a paste to a relatively solid material). In some examples, the mechanical connection formed via thick film conductive paste may be supplemented by using another types of mechanical connection, e.g., solder, in combination with thick film conductive paste 48.

In some examples, as shown in FIGS. 4A and 4B, thick film conductive paste 48a, 48b, 48c may be disposed between interior-facing feedthrough conductive pads 46 and exterior-facing filter conductive pads 60. Thick film conductive paste 48a, 48b, 48c may take the place of, or be used in combination with a solder or other mechanical and electrical connection between interior-facing feedthrough conductive pads 46 and exterior-facing filter conductive pads 60.

Figure 5:
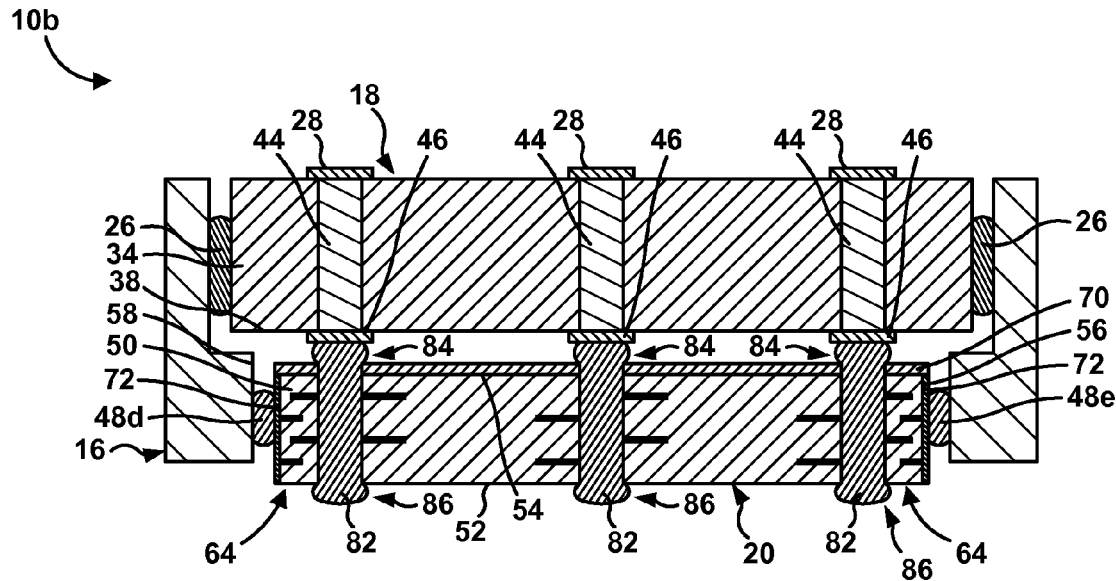
FIG. 5 is a cross-sectional view taken along section line A-A of FIG. 3 that illustrates another example configuration of a feedthrough assembly.

In some examples, capacitive filter array 20 may not include externally-facing filter conductive pads 60, filter conductive vias 62, and internally-facing filter conductive pads 32 (as does the example of filter array 20 shown in FIGS. 4A and 4B). Feedthrough assembly 10b shown in FIG. 5 is similar to feedthrough assembly 10a shown in FIGS. 4A and 4B. Some reference numerals have been omitted in FIG. 5 for sake of clarity; nevertheless, in some examples, feedthrough assembly 10b may be substantially similar to feedthrough assembly 10a, aside from the differences described herein. Compared to feedthrough assembly 10a shown in FIGS. 4A and 4B, feedthrough assembly 10b shown in FIG. 5 includes an example capacitive filter array 20 that includes filter array conductive pathways 82 formed of a thick film conductive paste, such as Ag—Pd, instead of externally-facing filter conductive pads 60, filter conductive vias 62, and internally-facing filter conductive pads 32.

As shown in FIG. 5, capacitive filter substrate 50 defines a plurality of passageways between internally facing side 52 and externally facing side 54. The thick film conductive paste is disposed in the plurality of passageways and forms filter array conductive pathways 82. Externally-facing ends 84 of filter array conductive pathways 82 may extend to or beyond externally facing side 54 of capacitive filter substrate 50. In this way, externally-facing ends 84 may electrically and mechanically connect to respective ones of internally-facing feedthrough conductive pads 46 (of feedthrough 18). Externally-facing ends 84 thus may mechanically connect capacitive filter array 20 to feedthrough 18.

Internally-facing ends 86 of filter array conductive pathways 82 may extend to or beyond internally facing side 52 of capacitive filter substrate 50. In this way, internally-facing ends 86 may be functionally similar to internally-facing filter conductive pads 32. For example, internally-facing ends 86 of filter array conductive pathways 82 may provide a location for electrically connecting respective electrical conductors that extend to circuitry within the IMD, such as sensing circuitry, therapy delivery circuitry, or the like.

Figure 6:
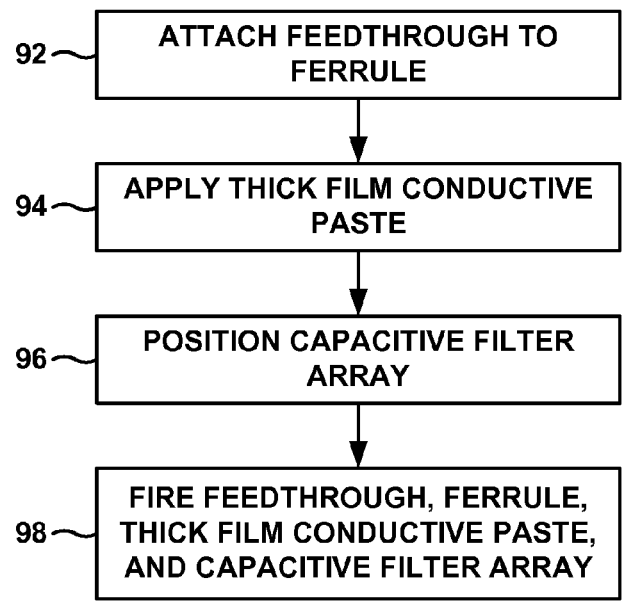
FIG. 6 is a flow diagram that illustrates an example technique for forming a feedthrough assembly that includes a thick film conductive paste.

FIG. 6 is a flow diagram that illustrates an example technique for forming a feedthrough assembly 10 that includes a thick film conductive paste. The technique illustrated in FIG. 6 will be described with concurrent reference to feedthrough assembly 10a shown in FIGS. 4A and 4B for clarity. However, it will be appreciated by those of skill in the art that the technique shown in FIG. 6 may be used to construct other feedthroughs.

The technique shown in FIG. 6 may include attaching feedthrough 18 to ferrule 16 (92). Feedthrough 18 may be connected to ferrule 16 using any technique that forms hermetic seal 26 between feedthrough 18 and ferrule 16. For example, ferrule 16 and feedthrough 18 may be connected using brazing, diffusion bonding, laser sintering of glass, or the like. Hermetic seal 26 may be formed using a biocompatible, biostable material. Examples of materials that may be used to form a hermetic seal 26 include gold, a nickel-gold alloy, platinum, platinum-iridium, or a biocompatible glass.

The technique also may include applying thick film conductive paste 48 to desired locations of feedthrough 18, ferrule 16, and/or capacitive filter array 20 (94). In some examples, the technique may include applying thick film conductive paste 48 to internally-facing feedthrough conductive pads 46. In other examples, the method may include applying thick film conductive paste 48 to externally-facing filter conductive pads 60. In other examples, the technique may include applying thick film conductive paste 48 to second interior wall 58 of ferrule 16. In other examples, the method may include applying thick film conductive paste 48 to perimeter conductive contact 72. In other examples, the technique may include applying thick film conductive paste 48 to internally-facing feedthrough conductive pads 46 and second interior wall 58. In other examples, the technique may include applying thick film conductive paste 48 to internally-facing feedthrough conductive pads 46 and perimeter conductive contact 72. In other examples, the technique may include applying thick film conductive paste 48 to externally-facing filter conductive pads 60 and second interior wall 58. In other examples, the technique may include applying thick film conductive paste 48 to externally-facing filter conductive pads 60 and perimeter conductive contact 72.

Thick film conductive paste 48 may be applied to the desired locations of feedthrough 18, ferrule 16, and/or capacitive filter array 20 (94) using any one or combination of a variety of techniques, including, for example, screen printing, brushing, using a dispenser, or the like. Thick film conductive paste 48 may initially be in paste form (e.g., a suspension of a powder mixture of Ag, Pd, and, optionally, glass frit in a liquid carrier). In some examples, the amount of liquid carrier may be selected such that thick film conductive paste 48 is relatively viscous and does not flow readily from the locations at which it is applied (after application). For example, thick film conductive paste may have a viscosity of between about 100 kilocentipoise (kcps; about 1,000 poise) and about 250 (kcps; about 2,500 poise).

Once the thick film conductive paste 48 has been applied to the desired locations of feedthrough 18, ferrule 16, and/or capacitive filter array 20 (94), capacitive filter array 20 may be positioned in a desired orientation relative to ferrule 16 and feedthrough 18 (96). For example, this may include positioning capacitive filter array 20 such that externally-facing filter array side 54 is proximate (near) to internally-facing feedthrough side 38 (e.g., so that, in examples in which thick film conductive paste 48 is used to electrically connect internally-facing feedthrough conductive pads 46 and externally-facing filter array conductive pads 60, thick film conductive paste 48a, 48b, 48c is contacting both internally-facing feedthrough conductive pads 46 and externally-facing filter array conductive pads 60). This may also include positioning capacitive filter array 20 such that capacitive filter perimeter 56 is proximate (near) to second interior wall 58 of ferrule 16 (e.g., so that, in examples in which thick film conductive paste 48 is used to electrically connect perimeter conductive contact 72 and second interior wall 56, thick film conductive paste 48d and 48e are contacting both perimeter conductive contact 72 and second interior wall 56).

After capacitive filter array 20 has been positioned in the desired orientation relative to ferrule 16 and feedthrough 18 (96), feedthrough assembly 10a may be heated to convert thick film conductive paste 48 from a paste to a relatively solid (e.g., an Ag—Pd alloy with glass frit) material (98). For example, feedthrough assembly 10a may be heated at a temperature between about 700° C. and about 850° C. for between about 30 minutes and about 60 minutes, with about 10 minutes of substantially constant temperature at the peak temperature. By heating feedthrough assembly 10a and converting thick film conductive paste 48 to a relatively solid material, mechanical and electrical connection may be made between respective ones of internally-facing feedthrough conductive pads 46 and respective ones of externally-facing filter array conductive pads 60, which may result in mechanical connection between feedthrough 18 and capacitive filter array 20. Similarly, heating feedthrough assembly 10a and converting thick film conductive paste 48 to a relatively solid material may make mechanical and electrical connection between perimeter conductive contact 72 and second interior wall 58, which may result in mechanical connection between ferrule 16 and capacitive filter array 20.

Figure 7:
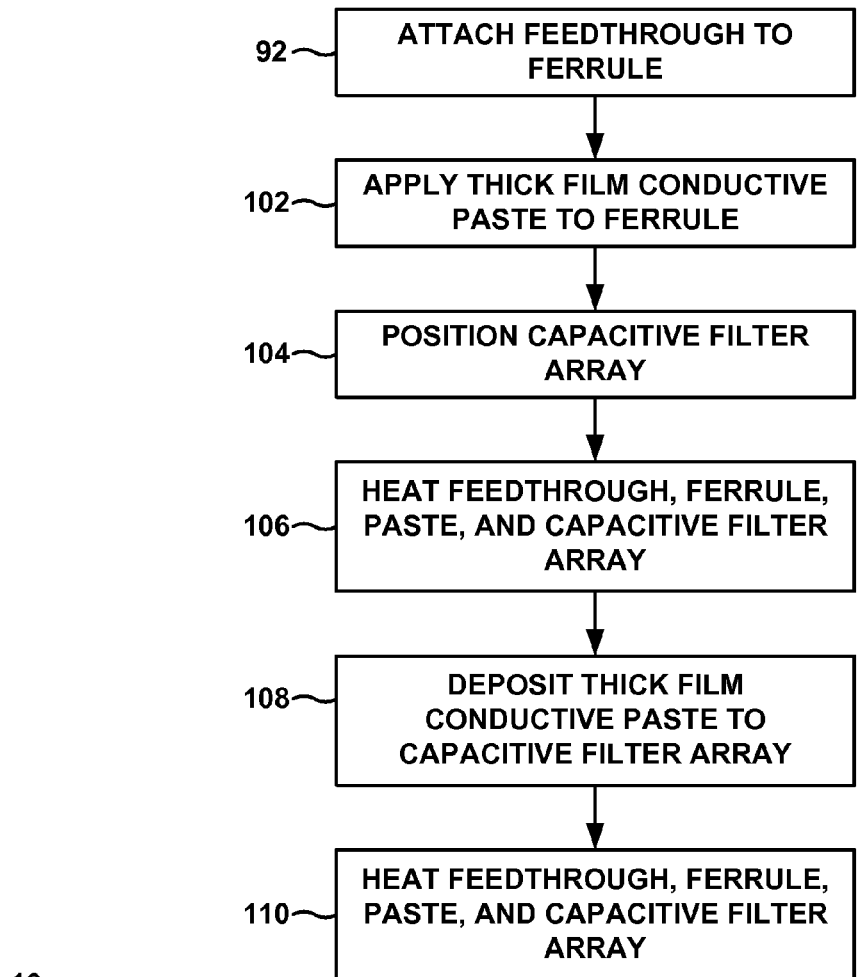
FIG. 7 is a flow diagram that illustrates another example technique for forming a feedthrough assembly that includes a thick film conductive paste.

FIG. 7 is a flow diagram that illustrates another example technique for forming a feedthrough assembly in accordance with aspects of this disclosure. The example technique shown in FIG. 7 will be described with concurrent reference to feedthrough assembly 10b shown in FIG. 5. The technique shown in FIG. 7 may include attaching feedthrough 18 to ferrule 16 (92). Feedthrough 18 may be connected to ferrule 16 using any technique that forms hermetic seal 26 between feedthrough 18 and ferrule 16. For example, ferrule 16 and feedthrough 18 may be connected using brazing, diffusion bonding, laser sintering of glass, or the like. Hermetic seal 26 may be formed using a biocompatible, biostable material. Examples of materials that may be used to form a hermetic seal 26 include gold, a nickel-gold alloy, platinum, platinum-iridium, or a biocompatible glass.

The technique shown in FIG. 7 also includes applying thick film conductive paste 48d, 48e to second interior wall 58 of ferrule 16 (102). Alternatively, thick film conductive paste 48d, 48e may be applied to perimeter conductive contact 72 of capacitive filter array 20 (102). Thick film conductive paste 48d, 48e may be applied to second interior wall 58 and/or perimeter conductive contact 72 (102) using any one or combination of a variety of techniques, including, for example, screen printing, brushing, using a dispenser, or the like. Thick film conductive paste 48d, 48e may initially be in paste form (e.g., a suspension of a powder mixture of Ag, Pd, and, optionally, glass frit in a liquid carrier). In some examples, the amount of liquid carrier may be selected such that thick film conductive paste 48d, 48e is relatively viscous and does not flow readily from the locations at which it is applied (after application). For example, thick film conductive paste may have a viscosity of between about 100 kilocentipoise (kcps; about 1,000 poise) and about 250 (kcps; about 2,500 poise).

Once thick film conductive paste 48d, 48e has been applied to second interior wall 58 and/or perimeter conductive contact 72 (102), capacitive filter array 20 may be positioned in a desired orientation relative to ferrule 16 and feedthrough 18 (104). For example, this may include positioning capacitive filter array 20 such that externally-facing filter array side 54 is proximate (near) to internally-facing feedthrough side 38. In some examples, externally-facing filter array side 54 may be positioned near to internally-facing feedthrough side 38 with a space or gap between externally-facing filter array side 54 and internally-facing feedthrough side 38. In other examples, externally-facing filter array side 54 may be positioned near to internally-facing feedthrough side 38 with substantially no space or gap between externally-facing filter array side 54 and internally-facing feedthrough side 38 (e.g., electrical insulation layer 70 may contact internally-facing feedthrough side 38, internally-facing feedthrough conductive pads 46, or an electrically insulating material disposed on internally-facing feedthrough side 38). Positioning capacitive filter array 20 in a desired orientation relative to ferrule 16 and feedthrough 18 (104) may also include positioning capacitive filter array 20 such that capacitive filter perimeter 56 is proximate (near) to second interior wall 58 of ferrule 16 (e.g., so that thick film conductive paste 48d and 48e are contacting both perimeter conductive contact 72 and second interior wall 56).

In some examples, the technique may optionally include heating ferrule 16, feedthrough 18, capacitive filter array 20, and thick film conductive paste 48d and 48e to convert thick film conductive paste 48d and 48e from a paste to a relatively solid material and mechanically and electrically connect capacitive filter array 20 to ferrule 16 using thick film conductive paste 48d and 48e (106). In other examples, the technique may not include step (106). For example, feedthrough assembly 10b may be heated at a temperature between about 700° C. and about 850° C. for between about 30 minutes and about 60 minutes, with about 10 minutes of substantially constant temperature at the peak temperature.

Regardless of whether the technique includes step (106), the technique proceeds with depositing thick film conductive paste within passageways through capacitive filter substrate 50 to form filter array conductive pathways 82 (108). As described above, thick film conductive paste may be deposited using any one or combination of a variety of techniques, including, for example, screen printing, brushing, using a dispenser, or the like. The thick film conductive paste may initially be in paste form (e.g., a suspension of a powder mixture of Ag, Pd, and, optionally, glass frit in a liquid carrier). In some examples, the amount of liquid carrier may be selected such that the thick film conductive paste is relatively viscous and does not flow readily from the locations at which it is applied (after application). For example, thick film conductive paste may have a viscosity of between about 100 kilocentipoise (kcps; about 1,000 poise) and about 250 (kcps; about 2,500 poise).

Sufficient thick film conductive paste may be applied within the passageways through capacitive filter substrate 50 to result in externally-facing ends 84 contacting internally-facing feedthrough conductive pads 46. In some examples, this may result in externally-facing ends 84 extending beyond externally-facing filter array side 54 (and/or electrically insulating layer 70). In other examples, such as when there is substantially no space or gap between electrically insulating layer 70 and internally-facing feedthrough side 38, externally-facing ends 84 may not extend beyond externally-facing filter array side 54 (and/or electrically insulating layer 70). Additionally or alternatively, sufficient thick film conductive paste may be applied within the passageways through capacitive filter substrate 50 to result in internally-facing ends 86 extending to or beyond internally-facing filter array side 52.

The example technique of FIG. 7 also includes heating ferrule 16, feedthrough 18, capacitive filter array 20, filter array conductive pathways 82, and thick film conductive paste 48d and 48e to convert thick film conductive paste 48d and 48e and filter array conductive pathways 82 from a paste to a relatively solid material (110). In some examples in which the technique includes step (106), the heating step (110) may not convert thick film conductive paste 48d and 48e from a paste to a relatively solid material, as thick film conductive paste 48d and 48e may already be a relatively solid material.

In some examples, feedthrough assembly 10b may be heated at a temperature between about 700° C. and about 850° C. for between about 30 minutes and about 60 minutes, with about 10 minutes of substantially constant temperature at the peak temperature. By heating feedthrough assembly 10b and converting filter array conductive pathways 82 to a relatively solid material, mechanical and electrical connection may be made between respective ones of internally-facing feedthrough conductive pads 46 and filter array conductive pathways 82, which may result in mechanical connection between feedthrough 18 and capacitive filter array 20.

Thick film conductive paste is one example of a material that may be used to mechanically and electrically connect feedthrough 18 and capacitive filter array 20, and capacitive filter array 20 and ferrule 16. However, in other example, other structures may be used to electrically and mechanically connect the respective structures. For example, in accordance with some aspects of the disclosure, a lead frame assembly may be used to make mechanical and electrical connection between feedthrough 18 and capacitive filter array 20 and/or between capacitive filter array 20 and ferrule 16.

FIG. 8 illustrates an example feedthrough assembly 10c in which a lead frame assembly 116 mechanically and electrically connects feedthrough 18 and capacitive filter array 20 and capacitive filter array 20 and ferrule 16. In FIG. 8, lead frame assembly 116 is formed by a combination of electrically conductive leads 114a, 114b, 114c, and 114d (collectively, "electrically conductive leads 114").

In some examples, feedthrough assembly 10c is substantially similar to feedthrough assemblies 10a and 10b described with reference to FIGS. 4A, 4B, and 5, except for the differences noted herein. Similar to FIG. 5, certain reference numerals shown in FIGS. 4A and 4B are omitted from FIG. 8 for the sake of clarity.

As shown in FIG. 8, lead frame assembly 116 mechanically and electrically connects feedthrough 18 and capacitive filter array 20. Lead frame assembly 116 may include a first electrically conductive lead 114a, a second electrically conductive lead 114b, and a third electrically conductive lead 114c, which electrically connect respective ones of filter conductive vias 62 with respective ones of internally-facing feedthrough conductive pads 46. Lead frame assembly 116 also may include fourth electrically conductive lead 114d, which electrically connects perimeter conductive contact 72 with ferrule 16.

Each of electrically conductive leads 114 may be formed of an electrical conductive metal, such as niobium; titanium; titanium alloys such as titanium-6Al-4V or titanium-vanadium; platinum; molybdenum; zirconium; tantalum; vanadium; tungsten; iridium; rhodium; rhenium; osmium; ruthenium; palladium; silver; and alloys, mixtures, and combinations thereof. In some examples, at least some of electrically conductive leads 114 possess sufficient mechanical strength to allow first electrically conductive lead 114a, second electrically conductive lead 114b, and/or third electrically conductive lead 114c to maintain a gap between electrically insulating layer 70 formed on externally-facing filter array side 54 and feedthrough electrically insulating layer 112 formed on internally-facing feedthrough side 38. In some examples, electrically conductive leads 114 may include bare metal (e.g., with no electrical insulation formed on a surface of electrically conductive leads 114). In other examples, at least one of electrically conductive leads 114 may include electrical insulation formed on a surface of the at least one of electrically conductive leads 114, such as an electrically insulating polymer.

FIG. 8 illustrates three filter conductive vias 62 and corresponding first electrically conductive lead 114a, second electrically conductive lead 114b, and third electrically conductive lead 114c. However, in other examples, as described above, capacitive filter array may include fewer than three filter conductive vias 62 or more than three filter conductive vias 62. In some such examples, feedthrough assembly 10c may include a corresponding number of electrically conductive leads 114 (e.g., one electrically conductive lead 114 for each filter conductive vias 62).

Additionally or alternatively, as described above, capacitive filter array 20 may include a single perimeter conductive contact 72, which may extend at least partially (or substantially fully) around capacitive filter perimeter 56, or capacitive filter array 20 may include a plurality of discrete perimeter conductive contacts 72 (e.g., one perimeter conductive contact 72 for each one of filter conductive vias 62). In either example, although FIG. 8 illustrates one electrically conductive lead (fourth electrically conductive lead 114d) connecting perimeter conductive contact 72 to ferrule 16, in other implementations, feedthrough assembly 10c may include more than one electrically conductive lead connecting perimeter conductive contact 72 to ferrule 16. For example, feedthrough assembly 10c may include a plurality of electrically conductive leads 114 that connect a single perimeter conductive contact 72 to ferrule 16. As another example, feedthrough assembly 10c may include a plurality of electrically conductive leads 114 that connect a plurality of discrete perimeter conductive contacts 72 to ferrule 16 (e.g., one electrically conductive lead 114 for each discrete perimeter conductive contact 72 or more than one electrically conductive lead 114 for each discrete perimeter conductive contact 72).

Figure 9:
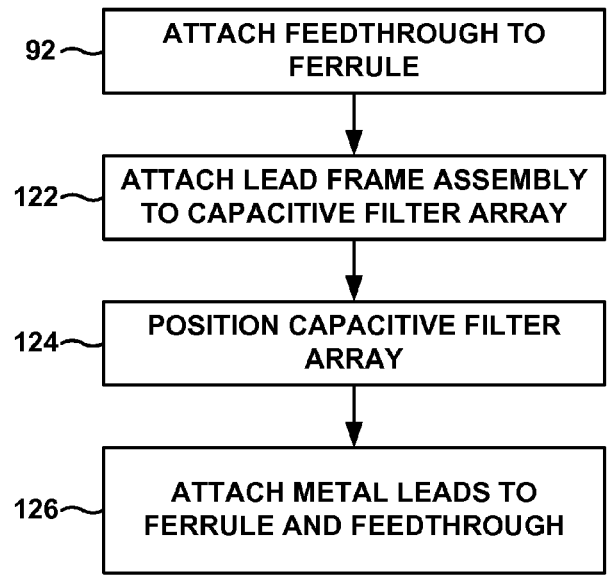
FIG. 9 is a flow diagram that illustrates another example technique for forming a feedthrough assembly that includes a lead frame assembly.

FIG. 9 is a flow diagram that illustrates an example technique for forming feedthrough assembly 10c. Although the technique of FIG. 9 will be described with reference to feedthrough assembly 10c shown in FIG. 8, one of ordinary skill will appreciate that the technique of FIG. 9 may be used to construct other feedthrough assemblies.

The technique of FIG. 9 includes attaching feedthrough 18 to ferrule 16 (92). As described above, feedthrough 18 may be connected to ferrule 16 using any technique that forms hermetic seal 26 between feedthrough 18 and ferrule 16. For example, ferrule 16 and feedthrough 18 may be connected using brazing, diffusion bonding, laser sintering of glass, or the like. Hermetic seal 26 may be formed using a biocompatible, biostable material. Examples of materials that may be used to form a hermetic seal 26 include gold, a nickel-gold alloy, platinum, platinum-iridium, or a biocompatible glass.

The technique shown in FIG. 9 also includes attaching lead frame assembly 116 to capacitive filter array 20 (122). In some examples, attaching lead frame assembly 116 includes attaching first electrically conductive lead 114a directly to a first one of filter conductive vias 62, attaching second electrically conductive lead 114b directly to a second one of filter conductive vias 62, attaching third electrically conductive lead 114c directly to a third one of filter conductive vias 62, and attaching fourth electrically conductive lead 114d to perimeter conductive contact 72. In other examples, capacitive filter array 20 may include a plurality of externally-facing filter conductive pads 60 (see FIGS. 4A and 4B), and first electrically conductive lead 114a, second electrically conductive lead 114b, and third electrically conductive lead 114c may be attached to respective ones of externally-facing filter conductive pads 60.

Electrically conductive leads 114 may be attached to capacitive filter array 20 using a variety of techniques. For example, electrically conductive leads 114 may be attached to capacitive filter array 20 using laser welding, parallel gap welding, thermosonic bonding, diffusion bonding, ultrasonic welding, opposed gap welding, laser brazing, step gap resistance welding, percussion arc welding, or soldering (conventional or laser).

In other examples, electrically conductive leads 114 may be attached to capacitive filter array 20 using a firing process. In a firing process, capacitive filter array 20 and metals leads 114 may be heated to a temperature between about 700° C. and about 850° C. for between about 30 minutes and about 60 minutes, with about 10 minutes of substantially constant temperature at the peak temperature. The heating process may result in a mechanical connection between electrically conductive leads 114 and filter conductive vias 62 and perimeter conductive contact 72.

Figure 10:
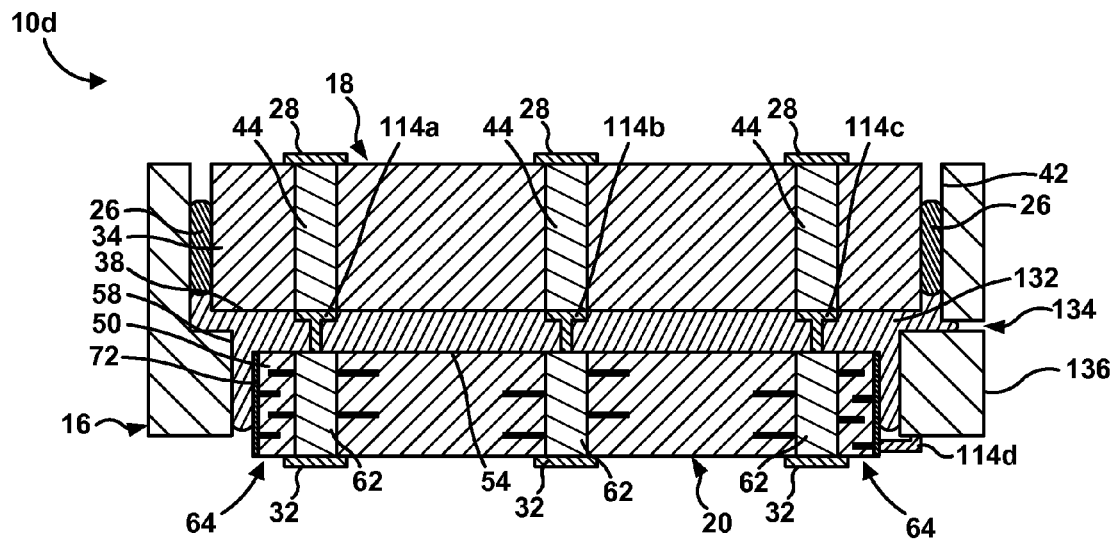
FIG. 10 is a cross-sectional view taken along section line A-A of FIG. 3 that illustrates another example configuration of a feedthrough assembly.

Once lead frame assembly 116 has been attached to capacitive filter array 20 (122), capacitive filter array 20 (including lead frame assembly 116) may be positioned in a desired position relative to ferrule 16 and feedthrough 18 (124). The desired position may include a position in which respective ones of electrically conductive leads 114 contact respective ones of internally-facing feedthrough conductive pads 46 and ferrule 16, as shown in FIG. 8. In some examples, as shown in FIG. 10, feedthrough 18 may not include internally-facing feedthrough conductive pads 46, and capacitive filter array 20 may be positioned so that respective ones electrically conductive leads 114 contact respective ones of feedthrough conductive vias 44.

In some examples, described above, metals leads 114a, 114b, and/or 114c may possess sufficient mechanical strength to maintain separation between capacitive filter array 20 and feedthrough 18 when capacitive filter array 20 is positioned in the desired position relative to ferrule 16 and feedthrough 18 (124). For example, as shown in FIG. 8, electrically conductive leads 114a, 114b, and/or 114c may be sufficiently long to result in formation of a gap 118 between electrically insulating layer 70 and feedthrough electrically insulating layer 112. In other examples, electrically conductive leads 114a, 114b, 114c may be shorter, such that electrically insulating layer 70 and feedthrough electrically insulating layer 112 contact each other when capacitive filter array 20 is positioned in the desired position relative to ferrule 16 and feedthrough 18 (124).

The desired position of capacitive filter array 20 relative to ferrule 16 may include positioning fourth electrically conductive lead 114d contacting ferrule 16. As described above, ferrule 16 may form a portion of an electrically conductive path between capacitive filter array 20 (e.g., plurality of capacitive filters 64) and the housing of the IMD in which feedthrough assembly 10c is used. In some examples, as shown in FIG. 8, fourth electrically conductive lead 114d may contact ferrule 16 at internally-facing ferrule side 22. In other examples, fourth electrically conductive lead 114d may contact ferrule 16 at a different position, such as, for example, second interior wall 58.

In some examples, ferrule 16 may include or consist essentially of an electrically conducting material, and fourth electrically conductive lead 114d may contact ferrule 16 at substantially any position of ferrule 16 (e.g., any position of ferrule 16 that will be positioned within a housing of an IMD once ferrule 16 is attached to the IMD). In other examples, some portions of ferrule 16 may include an electrically insulating material and other portions of ferrule 16 may include an electrically conducting material. In these examples, fourth electrically conductive lead 114d may contact ferrule 16 at a portion of ferrule that includes an electrically conducting material.

Once capacitive filter array 20 has been positioned in the desired position relative to ferrule 16 and feedthrough 18, electrically conductive leads 114 may be attached to respective portions of feedthrough 18 and ferrule 16 (126). For example, first electrically conductive lead 114a, second electrically conductive lead 114b, and third electrically conductive lead 114c may be attached to respective ones of internally-facing feedthrough conductive pads 46 (or respective ones of feedthrough conductive vias 44, as shown in FIG. 10) using laser welding, parallel gap welding, thermosonic bonding, diffusion bonding, ultrasonic welding, opposed gap welding, laser brazing, step gap resistance welding, brazed interposer, percussion arc welding, or soldering (conventional or laser). Fourth electrically conductive lead 114d may be attached to ferrule 16 using a similar process.

In accordance with some aspects of the disclosure, an electrically insulating material may be introduced between capacitive filter array 20 and feedthrough 18 after feedthrough 18, capacitive filter array 20 and ferrule 16 have been assembled (e.g., using a backfill or underfill process).

Figure 11:
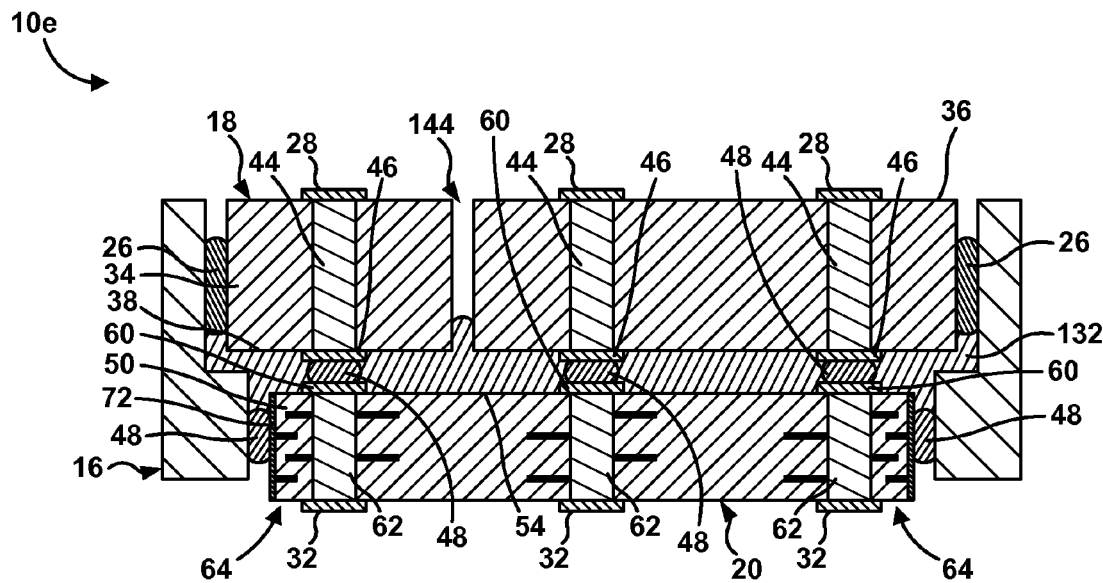
FIG. 11 is a cross-sectional view taken along section line A-A of FIG. 3 that illustrates a further example configuration of a feedthrough assembly.
Figure 12:
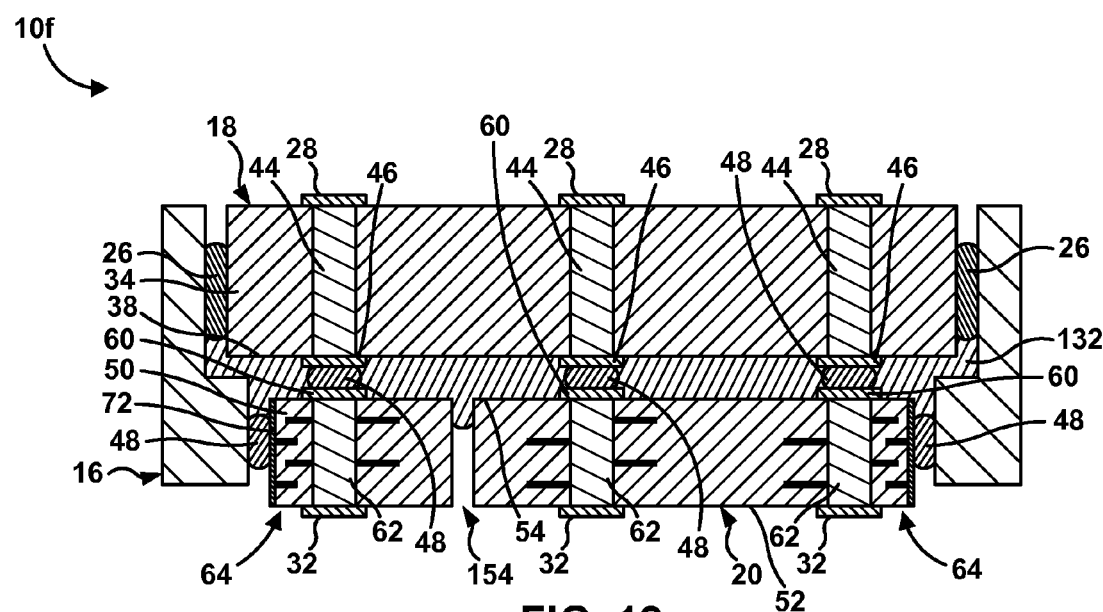
FIG. 12 is a cross-sectional view taken along section line A-A of FIG. 3 that illustrates an additional example configuration of a feedthrough assembly.

FIGS. 10-12 illustrate examples of feedthrough assemblies that include electrically insulating material introduced, e.g., using a backfill or underfill process.

In some examples, feedthrough assembly 10*d* may be similar to or substantially the same as feedthrough assembly 10*c* shown in FIG. 8, aside from the differences noted herein. Feedthrough assembly 10*d* includes first electrically conductive lead 114*a*, second electrically conductive lead 114*b*, and third electrically conductive lead 114*c*, which electrically and mechanically collect respective ones of filter conductive vias 62 with respective ones of feedthrough conductive vias 44. As described above with respect to FIG. 8, in some examples, feedthrough 18 may include internally-facing feedthrough conductive pads 46 and/or capacitive filter array 20 may include externally-facing filter conductive pads 60.

Feedthrough assembly 10*d* also includes an electrically insulating material 132 disposed between feedthrough 18 and capacitive filter array 20. Electrically insulating material 132 may extend substantially continuously between externally-facing filter array side 54 and internally-facing feedthrough side 38. Electrically insulating material 132 thus may electrically insulate metals leads 114 from one another, may electrically insulate electrically conductive leads 114 from perimeter conductive contact 72, and/or may electrically insulate electrically conductive leads 114*a*, 114*b*, and 114*c* from ferrule 16. In some examples, electrically insulating material 132 also may be disposed in the space between perimeter conductive contact 72 and ferrule 16, and may electrically insulate perimeter conductive contact 72 from ferrule 16.

In some examples, electrically insulating material 132 may contribute to mechanical connection between ferrule 16 and feedthrough 18, between feedthrough 18 and capacitive filter array 20, and/or between ferrule 16 and capacitive filter array 20.

Electrically insulating material 132 may include any suitable electrically insulating material. For example, electrically insulating material 132 may include an electrically non-conducting (i.e., electrically insulating) polyimide, epoxy, glass, or other electrically insulating polymer. Electrically insulating material 132 may be a material that can be introduced into the gap between internally-facing feedthrough side 38 and externally-facing feedthrough side 54 in a flowable state (e.g., a liquid or polymer melt), and then be converted into a substantially solid state (e.g., by cooling the material or removing a liquid/solvent from the material).

In some examples, electrically insulating material 132 may be introduced into the gap (e.g., gap 118 shown in FIG. 8) between internally-facing feedthrough side 38 and externally-facing feedthrough side 54 after capacitive filter array 20 has been attached to feedthrough 18 using electrically conductive leads 114*a*, 114*b*, and 114*c*. As shown in FIG. 10, ferrule 16 may define an underfill access channel 134. Underfill access channel 134 may be sized and positioned to allow introduction of electrically insulating material 132 into the gap between internally-facing feedthrough side 38 and externally-facing feedthrough side 54. For example, underfill access channel 134 may extend between an exterior wall 136 of ferrule 16 and first interior wall 42 of ferrule 16. In other examples, underfill access channel 134 may extend between exterior wall 136 and second interior wall 58.

Figure 14:
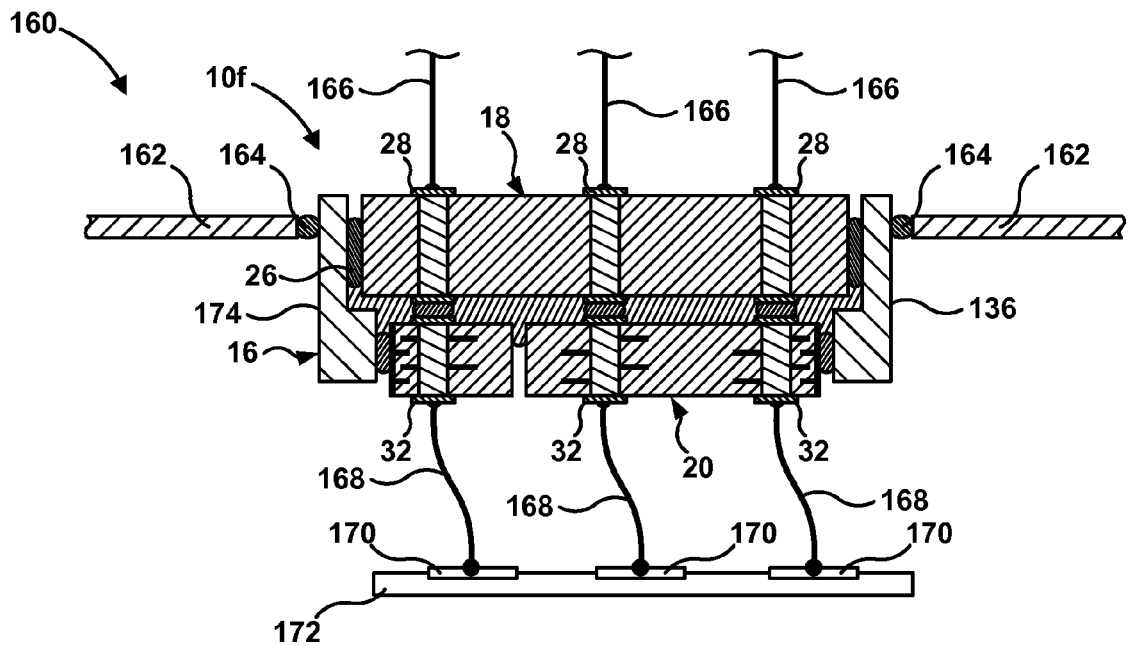
FIG. 14 is a conceptual diagram that illustrates an example feedthrough assembly attached to a housing of an IMD.

In some examples, as shown in FIG. 10, underfill access channel 134 may be located at a position of ferrule 16 that will be on an interior of a housing of an IMD in which feedthrough assembly 10*d* is used. This may promote a hermetic seal between the housing of the IMD and feedthrough assembly 10*d*, and prevent movement of fluids (e.g., bodily fluids) between an interior and an exterior of the IMD. Further details regarding attachment of an example feedthrough assembly to an IMD housing are shown in FIG. 14 and described below.

FIG. 11 is a cross-sectional diagram that illustrates another example feedthrough assembly 10*e*. Feedthrough assembly 10*e* may be similar to feedthrough assembly 10*a* illustrated in FIGS. 4A and 4B, aside from the differences noted herein. Feedthrough assembly 10*e* also includes an electrically insulating material 132 disposed between feedthrough 18 and capacitive filter array 20. Electrically insulating material 132 may extend substantially continuously between externally-facing filter array side 54 and internally-facing feedthrough side 38. Electrically insulating material 132 thus may electrically insulate the conductive pathways (e.g., including internally facing feedthrough conductive pads 46, thick film conductive paste 48, and externally-facing filter conductive pads 60) from one another, may electrically insulate the conductive pathways from perimeter conductive contact 72, and/or may electrically the conductive pathways from ferrule 16. In some examples, electrically insulating material 132 also may be disposed in the space between perimeter conductive contact 72 and ferrule 16, and may electrically insulate perimeter conductive contact 72 from ferrule 16.

As described above, electrically insulating material 132 may include any suitable electrically insulating material, such as an electrically non-conducting (i.e., electrically insulating) polyimide, epoxy, glass, or other electrically insulating polymer.

In some examples, electrically insulating material 132 may be introduced into the gap (e.g., gap 118 shown in FIG. 8) between internally-facing feedthrough side 38 and externally-facing feedthrough side 54 after capacitive filter array 20 has been attached to feedthrough 18 and ferrule 16 using thick film conductive paste 48. As shown in FIG. 11, feedthrough 18 may define an underfill access channel 144. Underfill access channel 144 may be sized and positioned to allow introduction of electrically insulating material 132 into the gap between internally-facing feedthrough side 38 and externally-facing feedthrough side 54. For example, underfill access channel 144 may extend between externally-facing feedthrough side 36 and internally-facing feedthrough side 38.

In some examples, as shown in FIG. 11, electrically insulating material 132 may form a hermetic seal with feedthrough 18, e.g., in underfill access channel 144. In other examples, feedthrough assembly 10*e* may include another material that forms a hermetic seal within underfill access channel 144, such as gold, a nickel-gold alloy, platinum, and platinum-iridium. This may promote a hermetic seal between the housing of the IMD and feedthrough assembly 10*e*, and prevent movement of fluids (e.g., bodily fluids) between an interior and an exterior of the IMD. Further details regarding attachment of an example feedthrough assembly to an IMD housing are shown in FIG. 14 and described below.

FIG. 12 is a cross-sectional diagram that illustrates another example feedthrough assembly 10*f*. Feedthrough assembly 10*e* may be similar to feedthrough assembly 10*a* illustrated in FIGS. 4A and 4B, aside from the differences noted herein. Feedthrough assembly 10*e* also includes an electrically insulating material 132 disposed between feedthrough 18 and capacitive filter array 20. Electrically insulating material 132 may extend substantially continuously between externally-facing filter array side 54 and internally-facing feedthrough side 38. Electrically insulating material 132 thus may electrically insulate the conductive pathways (e.g., including internally facing feedthrough conductive pads 46, thick film conductive paste 48, and externally-facing filter conductive pads 60) from one another, may electrically insulate the conductive pathways from perimeter conductive contact 72, and/or may electrically the conductive pathways from ferrule 16. In some examples, electrically insulating material 132 also may be disposed in the space between perimeter conductive contact 72 and ferrule 16, and may electrically insulate perimeter conductive contact 72 from ferrule 16.

In some examples, electrically insulating material 132 may be introduced into the gap (e.g., gap 118 shown in FIG. 8) between internally-facing feedthrough side 38 and externally-facing feedthrough side 54 after capacitive filter array 20 has been attached to feedthrough 18 and ferrule 16 using thick film conductive paste 48. As shown in FIG. 12, capacitive filter array 20 may define an underfill access channel 154. Underfill access channel 154 may be sized and positioned to allow introduction of electrically insulating material 132 into the gap between internally-facing feedthrough side 38 and externally-facing filter array side 54. For example, underfill access channel 154 may extend between internally-facing filter array side 52 and externally-facing filter array side 54. In some examples, positioning underfill access channel 154 in capacitive filter array 20 may promote a hermetic seal between the housing of the IMD and feedthrough assembly 10f, and prevent movement of fluids (e.g., bodily fluids) between an interior and an exterior of the IMD. Further details regarding attachment of an example feedthrough assembly to an IMD housing are shown in FIG. 14 and described below.

Figure 13:
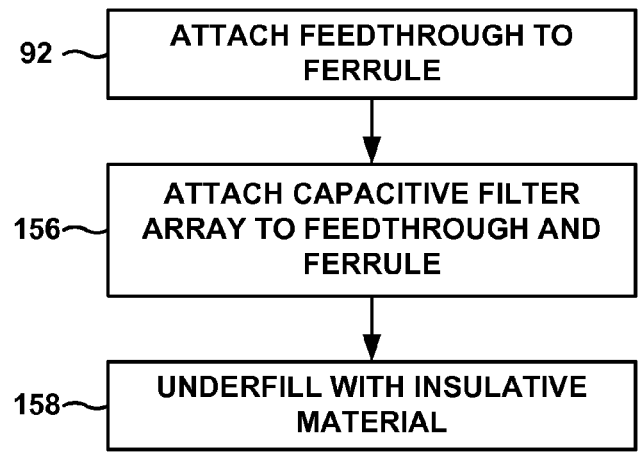
FIG. 13 is a flow diagram that illustrates an example technique for forming a feedthrough assembly.

FIG. 13 is a flow diagram that illustrates an example technique for forming a feedthrough assembly that includes an electrically insulating material between feedthrough 18 and capacitive filter array 20. The technique illustrated in FIG. 13 includes attaching feedthrough 18 to ferrule 16 (92). As described above, feedthrough 18 may be connected to ferrule 16 using any technique that forms hermetic seal 26 between feedthrough 18 and ferrule 16. For example, ferrule 16 and feedthrough 18 may be connected using brazing, diffusion bonding, laser sintering of glass, or the like. Hermetic seal 26 may be formed using a biocompatible, biostable material. Examples of materials that may be used to form a hermetic seal 26 include gold, a nickel-gold alloy, platinum, platinum-iridium, or a biocompatible glass.

The technique illustrated in FIG. 13 also includes attaching capacitive filter array 20 to feedthrough 18 and ferrule 16 (156). In some examples, as described above with respect to FIG. 6, attaching capacitive filter array to feedthrough 18 and ferrule 16 (156) may include applying thick film conductive paste 48 to desired locations of feedthrough 18, ferrule 16, and/or capacitive filter array 20 (94), positioning capacitive filter array 20 in a desired orientation relative to ferrule 16 and feedthrough 18 (96), and heating the feedthrough assembly (e.g., feedthrough assembly 10a, 10e, or 10f) to convert thick film conductive paste 48 from a paste to a relatively solid material (98). In other examples, as described above with respect to FIG. 7, attaching capacitive filter array to feedthrough 18 and ferrule 16 (156) may include applying thick film conductive paste 48d, 48e to second interior wall 58 of ferrule 16 or perimeter conductive contact 72 (102), positioning capacitive filter array 20 in a desired orientation relative to ferrule 16 and feedthrough 18 (104), heating thick film conductive paste 48d and 48e to convert thick film conductive paste 48d and 48e from a paste to a relatively solid material (106), depositing thick film conductive paste within passageways through capacitive filter substrate 50 to form filter array conductive pathways 82 (108), and heating ferrule 16, feedthrough 18, capacitive filter array 20, filter array conductive pathways 82, and thick film conductive paste 48d and 48e to convert thick film conductive paste 48d and 48e and filter array conductive pathways 82 from a paste to a relatively solid material (110). In other examples, as described above with respect to FIG. 9, attaching capacitive filter array to feedthrough 18 and ferrule 16 (156) may include attaching lead frame assembly 116 to capacitive filter array 20 (122), positioning capacitive filter array 20 (including lead frame assembly 116) in a desired position relative to ferrule 16 and feedthrough 18 (124), and attaching electrically conductive leads 114 to respective portions of feedthrough 18 and ferrule 16 (126).

Once capacitive filter array 20 has been attached to ferrule 16 and feedthrough 18, the gap (e.g., gap 118 shown in FIG. 8) between internally-facing feedthrough side 38 and externally-facing filter array side 54 may be underfilled with electrically insulating material 132 (158). As described above, electrically insulating material 132 may include a material that can be present in a flowable form, such as a liquid, suspension or polymer melt. Electrically insulating material 132 may be introduced into the gap between internally-facing feedthrough side 38 and externally-facing filter array side 54 through an underfill access channel, such as underfill access channel 134 defined by ferrule 16, underfill access channel 144 defined by feedthrough 20, or underfill access channel 154 defined by capacitive filter array 20. Once the flowable electrically insulating material 132 has been introduced into the gap between internally-facing feedthrough side 38 and externally-facing filter array side 54, electrically insulating material 132 may be converted to a substantially solid material, such as by cooling electrically insulating material 132 or removing a liquid carrier or solvent from electrically insulating material 132.

Any of the feedthrough assemblies 10 illustrated and described above may be utilized as a feedthrough assembly for an IMD. FIG. 14 is a conceptual diagram that illustrates an example feedthrough assembly attached to a housing of an IMD and electrically coupled to a plurality of leads and a plurality of electrical connections to circuitry. Although feedthrough assembly 10f is depicted in FIG. 14, any of the other feedthrough assemblies described herein may be utilized in an IMD in a similar manner.

IMD 160 includes a housing 162 and defines an opening in which feedthrough assembly 10f is disposed. Feedthrough assembly 10f is mechanically attached to a housing 162 of IMD 160 by a hermetic seal 164. For example, hermetic seal 164 may be formed between an exterior wall 136 of ferrule 16 and housing 162. Hermetic seal 164 may prevent bodily fluids of the patient from passing into the interior of IMD housing between ferrule 16 and housing 162, which could lead to damage to the internal electronics of the IMD 160. In one example, hermetic seal 164 comprises a braze joint between ferrule 16 and housing 162 (e.g., formed using laser brazing). In other examples, hermetic seal 164 may be formed using diffusion bonding. Examples of materials that may be used to form a hermetic seal 164 include any biocompatible, biostable material capable for forming a hermetic seal 164, such as, gold, a nickel-gold alloy, platinum, and platinum-iridium. Laser sintering of glass may also be used to bond ferrule 16 and housing 162.

In other examples, hermetic seal 164 may include a weld formed between housing 162 and ferrule 16. The weld may be formed of a material that is compatible with the material of housing 162 and the material of ferrule 16. As described above, in some examples, ferrule 16 may include titanium or a titanium alloy, and housing 162 also may include a titanium or titanium alloy. In some examples, the weld is formed using a laser welding process, e.g., to form a Ti—Ti weld.

In some examples, hermetic seal 164 may provide an electrical connection between housing 162 and ferrule 16 and may form a portion of the electrically conductive path between ground electrodes 68 of capacitive filter arrays 64 (see FIG. 4B) and housing 162. In some of these examples, housing 162 may act as an electrical ground for the signals filtered by capacitive filter arrays 64.

In some examples, IMD 160 may be device that is configured to deliver a therapy and/or monitor a physiologic condition of a patient. For example, IMD 160 may be a cardiac pacemaker, an implantable cardioverter/defibrillator, or an implantable neurostimulator, and may deliver therapy to or monitor physiologic signals from a patient's heart, muscle, nerve, brain, stomach, or another organ.

IMD 160 encloses circuitry, such as therapy delivery circuitry or sensing circuitry. Therapy delivery circuitry and/or sensing circuitry are represented in FIG. 14 as a printed board (PB) 172. Although not shown in FIG. 14, PB 172 may include electrical components, such as resistors, capacitor, inductors, batteries, integrated circuits, hybrid circuits, analog circuits, or the like mounted to or incorporated into PB 172. PB 172 also includes a plurality of contact pads 170, to which wires 168 are electrically connected.

Wires 168 electrically connect circuitry in or on PB 172 to internally-facing filter array conductive pads 32. Respective wires 168 may be electrically connected to respective contact pads 170 and respective internally-facing filter array conductive pads 32. Electrical connection between wires 168 and contact pads 170 and respective internally-facing filter array conductive pads 32 may be made by, for example, welding or soldering.

IMD 160 is also electrically connected to a plurality of lead conductors 166 via feedthrough assembly 10*f*. For example, respective ones of lead conductors 166 may be electrically connected to respective ones of externally-facing feedthrough conductive pads 28. Lead conductors 166 may be carried by at least one lead body, which may also carry electrodes, to which lead conductors 166 are electrically connected. Lead conductors 166 provide an electrical path through which IMD 160 may deliver electrical stimulation of a target tissue and/or sense physiologic signals from a target tissue.

Various examples have been described. These and other examples are within the scope of the following claims.

The invention claimed is:

1. A feedthrough assembly comprising:
a ferrule defining a ferrule opening;
a feedthrough at least partially disposed within the ferrule opening, wherein the feedthrough includes at least one feedthrough conductive pathway;
a capacitive filter array at least partially disposed within the ferrule opening, wherein the capacitive filter array includes at least one filter array conductive pathway; and
a lead frame assembly, wherein the lead frame assembly comprises an electrically conductive lead electrically connecting the at least one feedthrough conductive pathway and the at least one filter array conductive pathway, wherein the at least one feedthrough conductive pathway comprises an externally-facing feedthrough conductive pad positioned on an externally-facing side of the feedthrough, an internally-facing feedthrough conductive pad positioned on an internally-facing side of the feedthrough, and a feedthrough conductive via extending between the externally-facing feedthrough conductive pad and the internally-facing feedthrough conductive pad;
wherein the at least one filter array conductive pathway comprises an externally-facing filter conductive pad positioned on an externally-facing side of the capacitive filter array, an internally-facing filter conductive pad positioned on an internally-facing side of the capacitive filter array, and a filter conductive via extending between the externally-facing filter conductive pad and the internally-facing filter conductive pad;
wherein the electrically conductive lead electrically connects the internally-facing feedthrough conductive pad and the externally facing filter conductive pad.

2. The feedthrough assembly of claim 1, wherein the capacitive filter array further comprise a capacitive filter electrically coupled to the at least one filter array conductive pathway and a perimeter conductive contact electrically coupled to the capacitive filter.

3. The feedthrough assembly of claim 2, wherein the electrically conductive lead comprises a first electrically conductive lead, and wherein the lead frame assembly further comprises a second electrically conductive lead that electrically connects the perimeter conductive contact to the ferrule.

4. The feedthrough assembly of claim 1, wherein the capacitive filter array comprises a plurality of filter array conductive pathways, wherein the feedthrough comprises a plurality of feedthrough conductive pathways, wherein the lead frame assembly comprises a plurality of electrically conductive leads, and wherein respective ones of the plurality of electrically conductive leads electrically connect respective ones of filter array conductive pathways with respective ones of feedthrough conductive pathways.

5. The feedthrough assembly of claim 1, wherein the electrically conductive lead is fired to the at least one filter array conductive pathway.

6. The feedthrough assembly of claim 1, wherein the electrically conductive lead is soldered to the at least one feedthrough conductive pathway.

7. The feedthrough assembly of claim 1, wherein the electrically conductive lead is configured to maintain separation between the internally-facing side of the feedthrough and the externally-facing side of the capacitive filter array when the capacitive filter array is positioned in a desired position relative to the ferrule and the feedthrough.

8. The feedthrough assembly of claim 7, further comprising an electrically insulating material between the internally-facing side of the feedthrough and the externally-facing side of the capacitive filter array.

9. The feedthrough assembly of claim 8, wherein the electrically insulating material extends substantially continuously between the internally-facing side of the feedthrough and the externally-facing side of the capacitive filter array.

10. The feedthrough assembly of claim 8, further comprising an underfill access port defined by at least one of the ferrule, the capacitive filter array, or the feedthrough.

11. An implantable medical device comprising:
a housing defining an opening; and
a feedthrough assembly disposed in the opening and attached to the housing, wherein the feedthrough assembly comprises:
a ferrule defining a ferrule opening;
a feedthrough at least partially disposed within the ferrule opening, wherein the feedthrough includes at least one feedthrough conductive pathway,
a capacitive filter array at least partially disposed within the ferrule opening, wherein the capacitive filter array includes at least one filter array conductive pathway, and
a lead frame assembly, wherein the lead frame assembly comprise a electrically conductive lead electrically connecting the at least one feedthrough conductive pathway and the at least one filter array conductive pathway, wherein the at least one feedthrough conductive pathway comprises an externally-facing feedthrough conductive pad positioned on an externally-facing side of the feedthrough, an internally-facing feedthrough conductive pad positioned on an internally-facing side of the feedthrough, and a feedthrough conductive via extending between the externally-facing feedthrough conductive pad and the internally-facing feedthrough conductive pad;

wherein the at least one filter array conductive pathway comprises an externally-facing filter conductive pad positioned on an externally-facing side of the capacitive filter array, an internally-facing filter conductive pad positioned on an internally-facing side of the capacitive filter array, and a filter conductive via extending between the externally-facing filter conductive pad and the internally-facing filter conductive pad;

wherein the electrically conductive lead electrically connects the internally-facing feedthrough conductive pad and the externally facing filter conductive pad.

12. The implantable medical device of claim 11, wherein the capacitive filter array further comprise a capacitive filter electrically coupled to the at least one filter array conductive pathway and a perimeter conductive contact electrically coupled to the capacitive filter.

13. The implantable medical device of claim 12, wherein the electrically conductive lead comprises a first electrically conductive lead, and wherein the lead frame assembly further comprises a second electrically conductive lead that electrically connects the perimeter conductive contact to the ferrule.

14. The implantable medical device of claim 11, wherein the capacitive filter array comprises a plurality of filter array conductive pathways, wherein the feedthrough comprises a plurality of feedthrough conductive pathways, wherein the lead frame assembly comprises a plurality of electrically conductive leads, and wherein respective ones of the plurality of electrically conductive leads electrically connect respective ones of filter array conductive pathways with respective ones of feedthrough conductive pathways.

15. The implantable medical device of claim 11, wherein the electrically conductive lead is fired to the at least one filter array conductive pathway.

16. The implantable medical device of claim 11, wherein the electrically conductive lead is soldered to the at least one feedthrough conductive pathway.

17. The implantable medical device of claim 11, wherein the electrically conductive lead is configured to maintain separation between the internally-facing side of the feedthrough and the externally-facing side of the capacitive filter array when the capacitive filter array is positioned in a desired position relative to the ferrule and the feedthrough.

18. The implantable medical device of claim 17, further comprising an electrically insulating material between the internally-facing side of the feedthrough and the externally-facing side of the capacitive filter array.

19. The implantable medical device of claim 18, wherein the electrically insulating material extends substantially continuously between the internally-facing side of the feedthrough and the externally-facing side of the capacitive filter array.

20. The implantable medical device of claim 18, further comprising an underfill access port defined by at least one of the ferrule, the capacitive filter array, or the feedthrough.

* * * * *